(12) United States Patent
Tsuchiya

(10) Patent No.: US 7,718,423 B2
(45) Date of Patent: May 18, 2010

(54) INCUBATOR FOR OBSERVATION BY MICROSCOPE

(75) Inventor: Hideharu Tsuchiya, Fujinomiya (JP)

(73) Assignee: Tokai Hit Co., Ltd., Fujinomiya-shi (JP)

( * ) Notice: Subject to any disclaimer, the term of this patent is extended or adjusted under 35 U.S.C. 154(b) by 1278 days.

(21) Appl. No.: 10/525,245

(22) PCT Filed: Mar. 26, 2003

(86) PCT No.: PCT/JP03/03704

§ 371 (c)(1),
(2), (4) Date: Feb. 22, 2005

(87) PCT Pub. No.: WO2004/021066

PCT Pub. Date: Mar. 11, 2004

(65) Prior Publication Data

US 2005/0248836 A1 Nov. 10, 2005

(30) Foreign Application Priority Data

Aug. 28, 2002 (JP) ............................ 2002-249547
Mar. 24, 2003 (JP) ............................ 2003-080329

(51) Int. Cl.
 C12M 1/34 (2006.01)
 C12M 3/00 (2006.01)
 G02B 21/26 (2006.01)
 G02B 21/34 (2006.01)
 G01N 21/01 (2006.01)

(52) U.S. Cl. ................... 435/288.7; 359/395; 359/398; 219/201; 219/521

(58) Field of Classification Search ............. 435/288.7; 359/395, 398; 219/200, 201, 521
See application file for complete search history.

(56) References Cited

U.S. PATENT DOCUMENTS

| 3,472,726 | A | * | 10/1969 | Scheidegger | 165/48.1 |
| 4,275,646 | A | * | 6/1981 | Barna | 99/323 |
| 4,301,252 | A | * | 11/1981 | Baker et al. | 435/303.1 |
| 4,436,385 | A | * | 3/1984 | Fischer et al. | 359/391 |
| 4,629,862 | A | * | 12/1986 | Kitagawa et al. | 219/200 |

(Continued)

FOREIGN PATENT DOCUMENTS

JP 57-56812 4/1982

(Continued)

Primary Examiner—William H Beisner
Assistant Examiner—Danielle Henkel
(74) Attorney, Agent, or Firm—Oliff & Berridge, PLC

(57) ABSTRACT

An incubator capable of observing an observed specimen in a dish 220 by a microscope while culturing the specimen, wherein light is radiated from a capacitor(C), passed through a hole 273 in a top plate 271, a hole 275a in a upper side plate 275 and a hole 277a in a lower side plate 277, and let into an objective lens (T), and the specimen put in the dish 220 is observed by the microscope, whereby the change of the specimen with elapse of time can be continuously observed or recorded on a videotape while culturing the observed specimen in the dish 220.

17 Claims, 24 Drawing Sheets

U.S. PATENT DOCUMENTS

| | | | |
|---|---|---|---|
| 4,762,405 A | | 8/1988 | Inoue et al. |
| 5,019,691 A | * | 5/1991 | Lai .............................. 219/432 |
| 5,181,382 A | * | 1/1993 | Middlebrook ................. 62/3.2 |
| 5,192,506 A | * | 3/1993 | Kureshy et al. ............... 422/64 |
| 5,241,415 A | * | 8/1993 | Argentieri et al. ........... 359/395 |
| 5,257,128 A | * | 10/1993 | Diller et al. ................. 359/395 |
| 5,552,321 A | * | 9/1996 | Focht ...................... 435/286.1 |
| 5,717,190 A | * | 2/1998 | Inoue ......................... 219/522 |
| 5,731,587 A | * | 3/1998 | DiBattista et al. ........ 250/443.1 |
| 6,056,342 A | * | 5/2000 | Chan ......................... 294/99.2 |

FOREIGN PATENT DOCUMENTS

| | | |
|---|---|---|
| JP | 62-125211 | 8/1987 |
| JP | 10-028576 | 2/1998 |

* cited by examiner

INCUBATOR FOR OBSERVATION BY MICROSCOPE

BACKGROUND OF THE INVENTION

The present invention relates to an incubator for observation by microscope. More particularly the invention relates to an incubator capable of observing a specimen while incubating the specimen on the stage of microscope.

DESCRIPTION OF THE PRIOR ART

In the field of biotechnology such as life engineering or biological engineering or pathology, it is necessary to observe though microscope, living specimen such as germs or bacteria with incubating them under controlled atmosphere on which the incubation conditions such as temperature, humidity, or concentration of given gas are maintained for the target specimen.

In the prior art, specimen are cultured in an container and the container is maintained in an incubator device. When the incubated specimen is observed through microscope, the specimen is picked up and disposed on the stage of the microscope.

However, there are many disadvantages in such method for observation. In addition that the method requires much labor and it is cumbersome to do it, it is impossible to observe and/or take picture of the specimen as it is being under the incubation conditions. That is, accurate observation cannot be effected since it is conducted under non-controlled conditions.

In order to solve the problem, the inventor had proposed a temperature-constant, transparent incubator for observation by microscope enabling observation of specimen with incubating on the stage of microscope (see Japanese patent laid open (kokai) public disclosure 10-28576/1998).

The incubator includes a box-shaped, shallow container of a size just suitable for the stage of microscope. The container also has a hinged lid at one side end, by which the container is opened and/closed. Each of the bottom and the top of the container has a transparent heater plate of glass. The container further comprises an evaporating dish for humidifying and an aperture for delivering carbon dioxide gas into the container.

In the incubator of such structure, the incubation conditions within the container can be adjusted as desired by humidifying through the evaporation of water contained in the dish, controlling the amount of carbon dioxide gas delivered through the aperture, and raising the temperature controlling the amount of heat generated through the heater plates. The transparent top and bottom plates make it possible to pass light ray therethrough so that specimen such as germs of bacteria being incubated within the container can be observed on the stage of microscope as it is being under the desired incubation conditions.

DISCLOSURE OF THE INVENTION

However, the above-mentioned incubator of the prior art has following disadvantages.
(1) It is impossible to use an evaporating dish of large capacity, since a large space within the incubator is already occupied by a sample container such as a dish. In other words, the capacity of the evaporating dish is limited. As a result, when observation is carried out under humidified conditions, the period for which continuous observation can be carried out is limited on the capacity of the evaporating dish. If the incubator is opened to supply water to the dish, the incubation conditions are broken.
(2) When inserting any tools into the sample container, it is necessary to open the incubator substantially completely. This is because the deep dish-shaped sample container is used. If the incubator is opened completely, the incubation conditions such as the humidity, the temperature, or the concentration of carbon dioxide are broken.
(3) When observing another portion of the sample put in the container, it is necessary to open the incubator and remove the sample container relative to the objective lens. If the incubator is opened, the incubation conditions are broken.
(4) As set forth above, if the sample container is put in and out of the incubator, the incubator must be opened. This will lead to breakdown of the incubation conditions.
(5) When adding drugs or chemicals to the specimen being incubated in the incubator, the incubator must be opened. This will lead to the breakdown of the incubation conditions.
(6) The more the magnification is increased in microscopic observation; the more the objective lens is to be brought closer to the specimen. In this connection, it is necessary to provide an aperture through the lid (the heater plate) of the incubator to insert the objective lens therethrough. However, it is also necessary to enlarge the diameter of the aperture sufficiently to enable the portion to be observed of the sample varied. Thus, large clearance is to be formed between the edge of the aperture and the objective lens so that the desired incubation conditions cannot be kept within the incubator.
(7) In the incubator of the prior art, water in the evaporating dish is adapted to be evaporated by the heat energy generated by the transparent conductive film of the thickness of micron order provided on the transparent heater plate of glass, so that generable heat energy may be insufficient to produce water vapor.

The present invention is provided to solve the above-mentioned problems. It is an object of the invention to provide a new incubator for observation by microscope. In the incubator in accordance with the invention, the incubation and observation of the specimen can be carried out on the stage of microscope, and any operation be carried out to the specimen without spoiling atmosphere generated under set conditions within the incubator.

SUMMARY OF THE INVENTION

These and other objects are achieved by the following incubators for observation by microscope.

There is provided a first aspect of a incubator for observation by microscope comprising: an upwardly water tank unit including a container-accommodating portion in which a specimen container such as a dish is to be placed removably at the central portion thereof and a water reservoir disposed around the container-accommodating portion; a lid for covering the upper end of the unit; a heater for heating the specimen container and the unit; and a means for supplying gas into an incubation space defined by the unit and the lid; each of the unit and the lid having at the central portion thereof a light ray transmitting portion for transmitting light ray upwardly or downwardly therethrough.

There is provided a second aspect of the incubator according to the first aspect 1, further comprising a means for supplying water into the reservoir from the outside of the unit.

There is provided a third aspect of the incubator according to the first or second aspect, wherein the heater is of a plate type heating the container from the bottom thereof, and the heater is also provided with a light ray transmitting portion at the position corresponding to those provided on the unit and the lid.

There is provided a forth aspect of the incubator according to the third aspect, wherein the heater has a laminate comprising upper and lower plates and a heating element interposed therebetween, a top plate disposed above the upper plate with a space from the upper plate, and a frame for supporting the laminate and the top plate.

There is provided a fifth aspect of the incubator according to any of the preceding claims, further comprising a nutrient medium supplying means for supplying nutrient medium into the container within the unit from outside thereof.

There is provided a sixth aspect of the incubator according to the fifth aspect, wherein the nutrient medium supplying means has a structure for enabling the replenishment of nutrient medium within the container without removing the lid of the unit.

There is provided a seventh aspect of the incubator according to any of the preceding claims, the container-accommodating portion further comprising a pair of container holders disposed across the central portion of the unit and adjustable the spacing between the holders as desired.

There is provided a eighth aspect of the incubator according to any of the preceding aspects, wherein the unit is adapted to be placed on the upper surface of the stage of the microscope so as not to contact with the plate type heater with a spacing defined therebetween, and the unit and the heater are separable.

There is provided a ninth aspect of the incubator according to the eighth aspect, further comprising fixtures for securing the unit on the upper surface to the stage of the microscope.

There is provided a 10th aspect of the incubator according to any of the preceding aspects, further comprising a means for varying the position of the specimen container by displacing the container horizontally on the accommodating portion from outside of the unit.

There is provided a 11th aspect of the incubator according to any of the preceding aspects, wherein an entrance opening is provided through the side wall of the unit for putting the container into and out of the accommodating portion, and a side closure member for closing and opening the entrance is also provided.

There is provided a 12th aspect of the incubator according to the 11th aspect, wherein the heater is adapted to be fit into a tool fitting hole so as to flush an upper surface of the heater on, which the container will be placed, with the upper surface of a portion of the stage of the microscope.

There is provided a 13th aspect of the incubator according to any of the preceding aspects, wherein the lid covering the upper end of the unit has one or more slots formed through which any operation will be carried out to the specimen, the position of each slot is offset from the region of the accommodating portion on which the specimen container is to be placed, the lid is adjusted to shift, while closing still the opening on the upper end of the unit, to displace the slots directly above the region of the accommodating portion on which the specimen container is to be placed.

There is provided a 14th aspect of the incubator according to any of the preceding aspects, wherein the lid covering the upper end of the unit has an aperture formed in the region of the accommodating portion on which the specimen container is to be placed, the aperture is covered with a cover plate being rest on the lid, the cover plate can be displaced relative to the upper surface of the lid within the predetermined range while closing the aperture, the cover has a hole formed therein for inserting the objective lens.

There is provided a 15th aspect of the incubator according to any of the preceding claims, wherein on the bottom surface of the water tank is provided a water tank heater.

There is provided a 16th aspect of the incubator according to any of the third to 15th aspects, wherein the heater for heating the specimen container and the water tank unit has a container placing portion at which a heating portion is formed of a transparent conductive film.

There is provided a 17th aspect of the incubator according to any of the preceding claims, wherein that the light ray transmitting portion of the lid closing the upper end of the unit has a heating portion formed of a transparent conductive film.

There is provided a 18th aspect of the incubator according to any of the preceding aspects, further comprising a means for securing the specimen container to urge the container against the objective lens, when interposing any oil or water between the objective lens of the microscope and the specimen container.

The first incubator assembly for observation by microscope, comprising the incubator according to any of the ninth to 17th aspects, and a jig assembly for securing the fixtures for the incubator in the desired position including a centering member and an outer jig member. The centering member is used to align the center of the water tank unit with the center of tool fitting hole. The outer jig member is fit around the peripheral portion of the unit to position the fixtures. After the center of the water tank unit is aligned with the center of tool fitting hole by the centering member, the fixture is in contact and fit around the outer jig member for positioning.

The second incubator assembly for observation by microscope, comprising the incubator according to any of the first to 17th aspects, and a specimen container accommodated within the incubator. The specimen container includes a body opened at its upper surface and a lid for covering the upper surface. The lid is provided integrally with a pair of protrusions for connecting tubes at its upper surface. The protrusion includes an aperture for connecting the tube. The protrusion further includes a channel extending from the aperture to the lower surface of the lid.

The third incubator assembly for observation by microscope, comprising the incubator according to the 11th or 12th aspect, and a tongs for putting the specimen container into and out of the incubator. The tongs includes a pair of arms formed of elastically deformable material connected at the rear ends or proximal ends thereof. These arms are crossed with each other at the crossing portion provided through the middle portion of these arms. The arms further include a pair of urging portions to have the arms approach with each other and close by the force generated by the elastic deformation of the material of the tongs. The portions between the urging portions and the crossing portions make a pair of parallel pinching portions, preventing the urging portions to be removed in more-closed direction from the given position.

The fourth incubator assembly for observation by microscope, comprising at least two selected from the jig assembly for securing the fixtures of the first assembly, the specimen container of the second assembly, the means for securing the specimen container of the 18th aspect, and the tool for clamping the specimen container of the third assembly.

BRIEF DESCRIPTION OF THE DRAWINGS

Further feature of the present invention will become apparent to those skilled in the art to which the present invention relates from reading the following specification with reference to the accompanying drawings, in which.

DETAILED DESCRIPTION OF THE INVENTION

Figure 1:
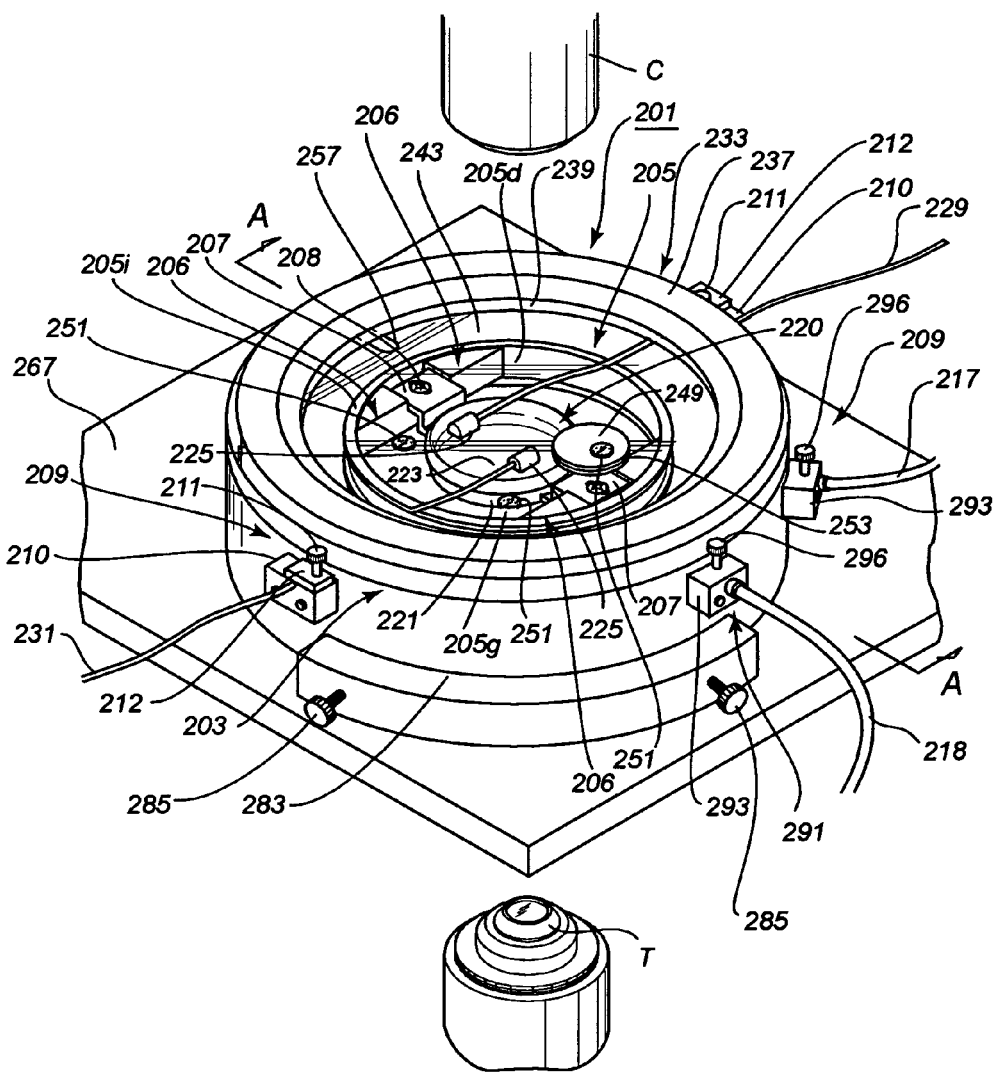
FIG. 1 is a perspective view showing the incubator for observation by microscope in accordance with the first embodiment of the present invention.
Figure 2:
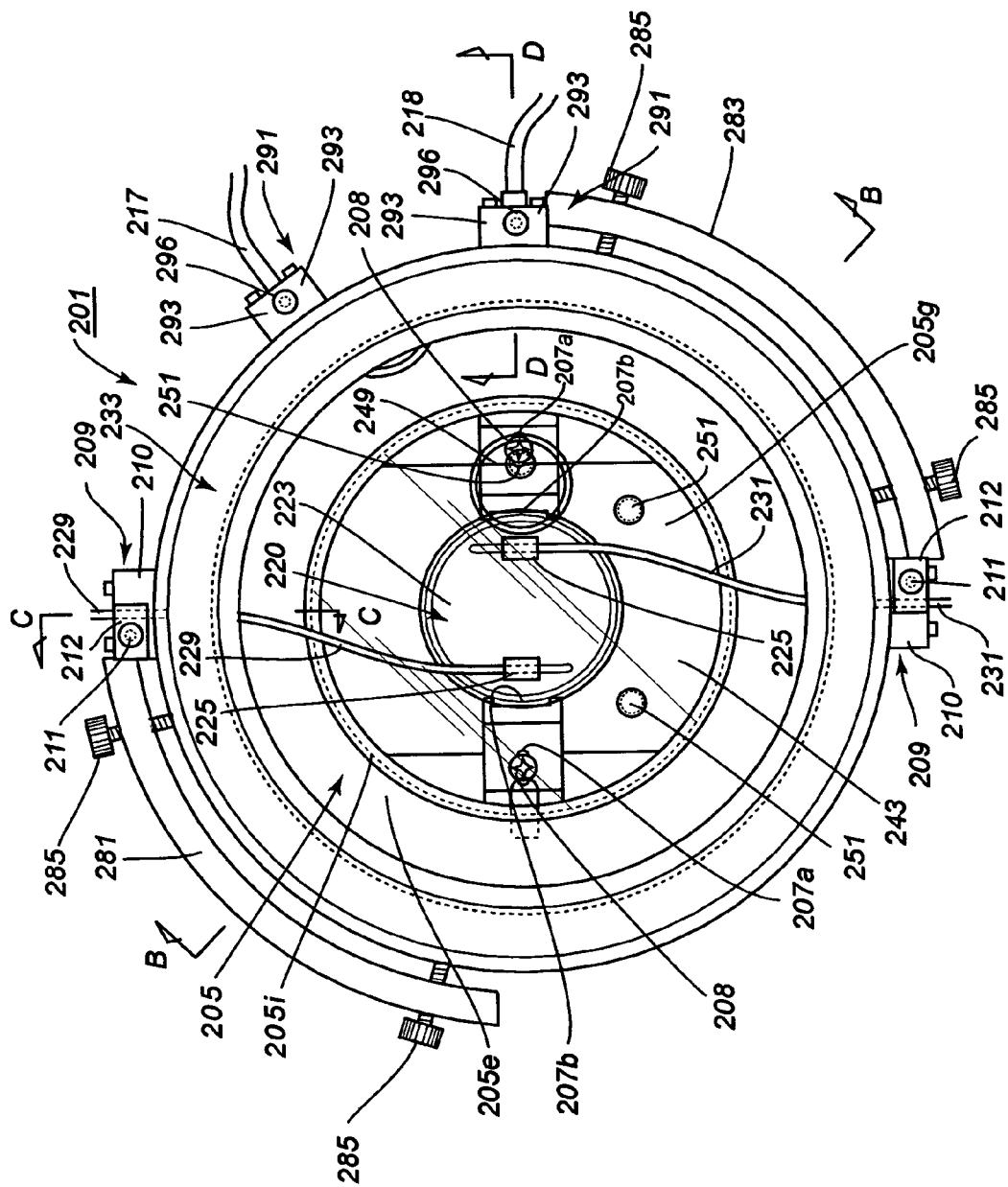
FIG. 2 is a plan view showing the incubator for observation by microscope in accordance with the first embodiment.
Figure 3:
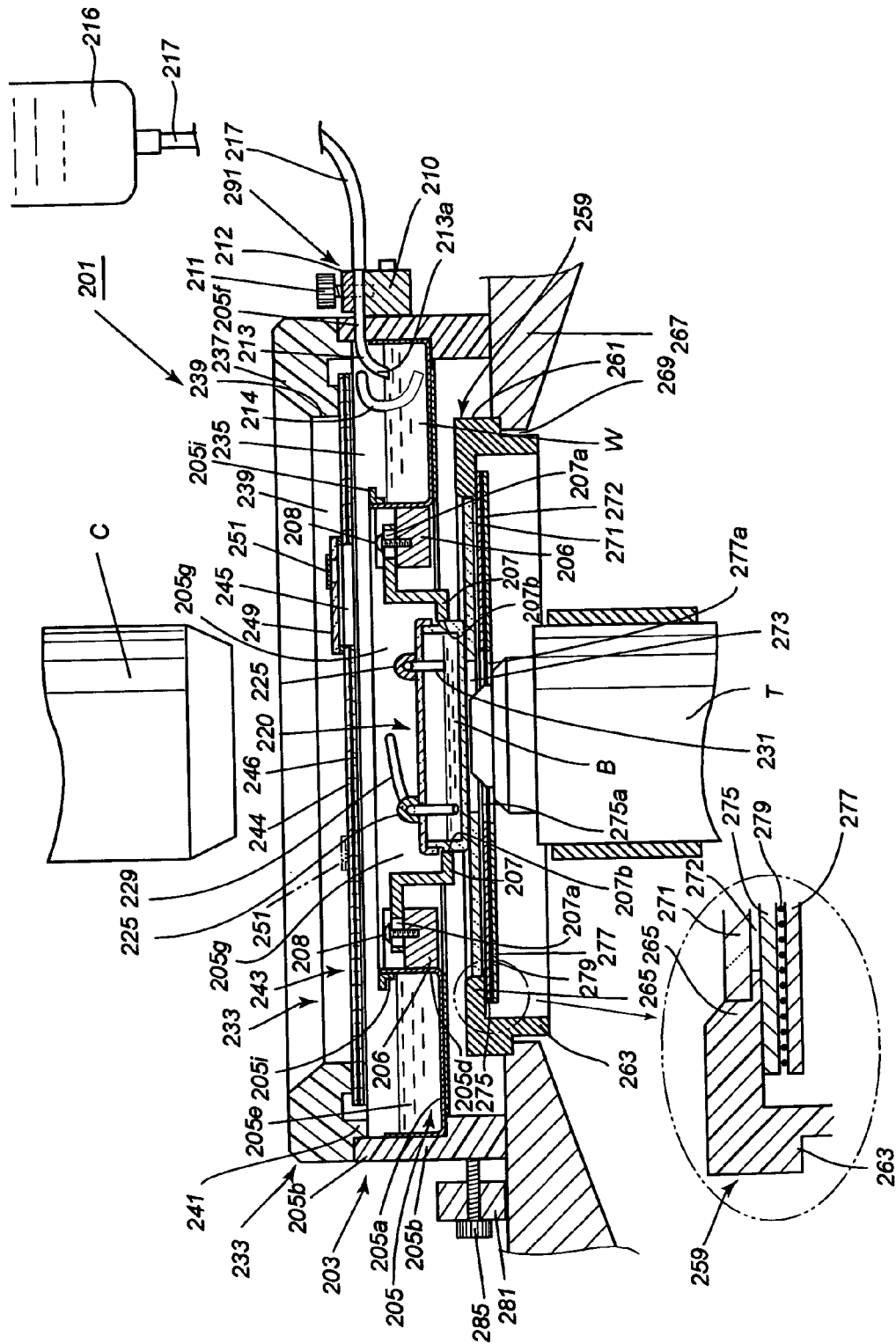
FIG. 3 is a partially cross sectional view taken substantially along line A-A of FIG. 1.
Figure 4:
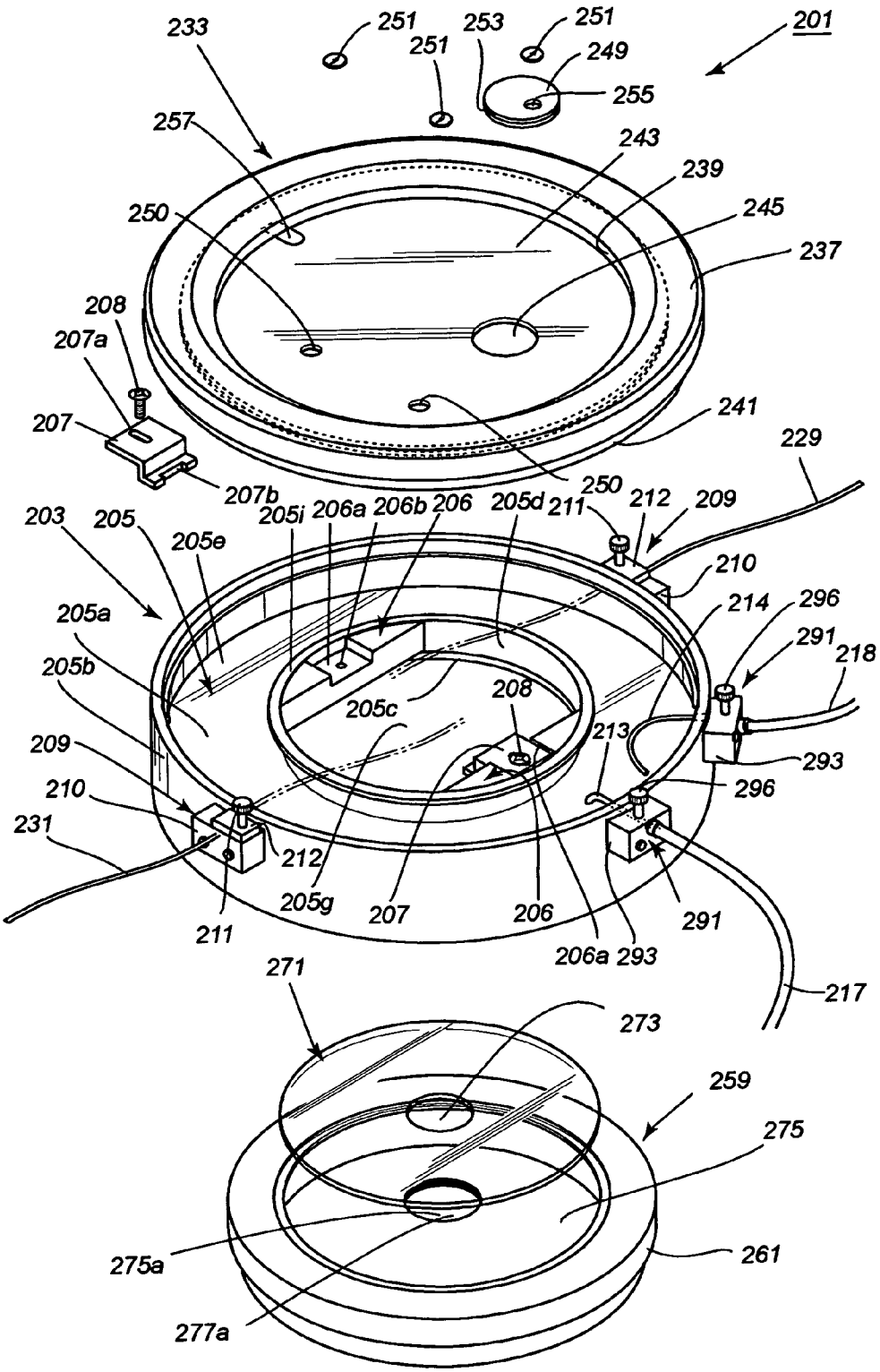
FIG. 4 is an exploded perspective view showing the incubator in accordance with the first embodiment.
Figure 5:
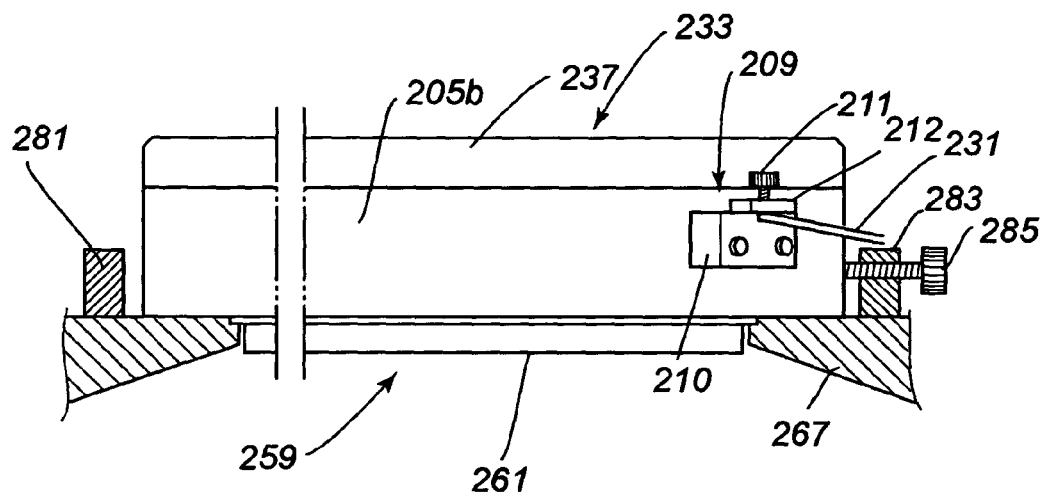
FIG. 5 is a partially eliminated enlarged cross sectional view taken along line B-B of FIG. 2.

An incubator 201 for observation by microscope in accordance with a first embodiment of the invention will now be described with reference to FIGS. 1-12. The incubator 201 is used in inverted microscope.

The incubator 201 includes a water tank unit 203 to which a dish 220 is to be detachably mounted, a lid 233 for covering the unit 203, a heater plate 259 for heating the unit 203 and the dish 220, and fixtures 281, 283 for securing the unit 203 on a stage 267 of a microscope.

Figure 10:
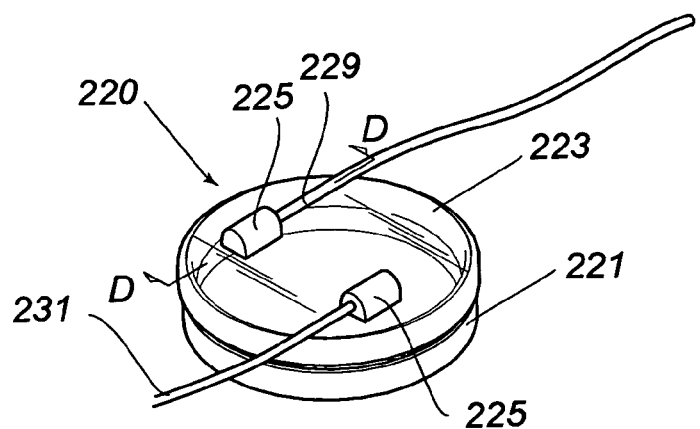
FIG. 10 is a perspective view showing an example of the dish used in the incubator in accordance with the first embodiment of the present invention.
Figure 11:
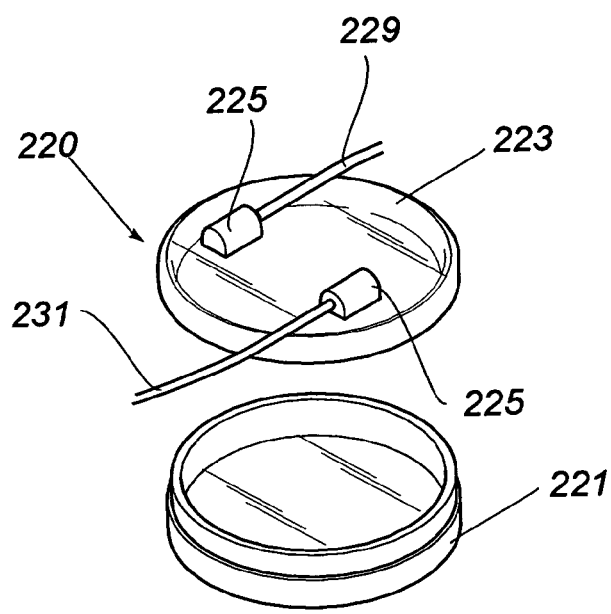
FIG. 11 is an exploded perspective view showing the container body and the lid of the dish.
Figure 12:
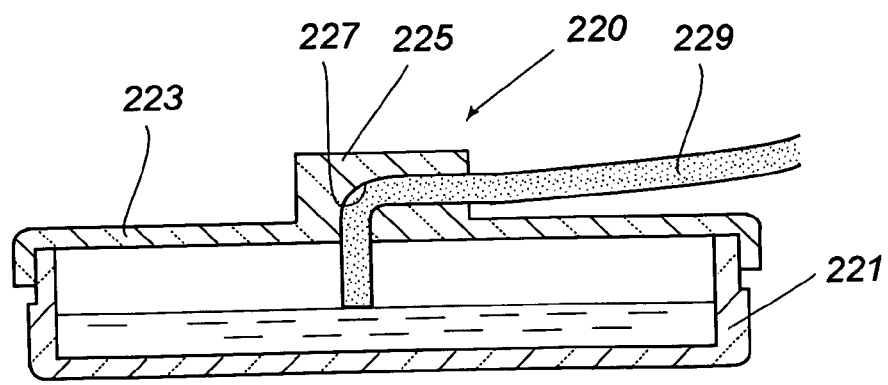
FIG. 12 is an enlarged cross sectional view taken substantially along line D-D of FIG. 10.
Figure 13:
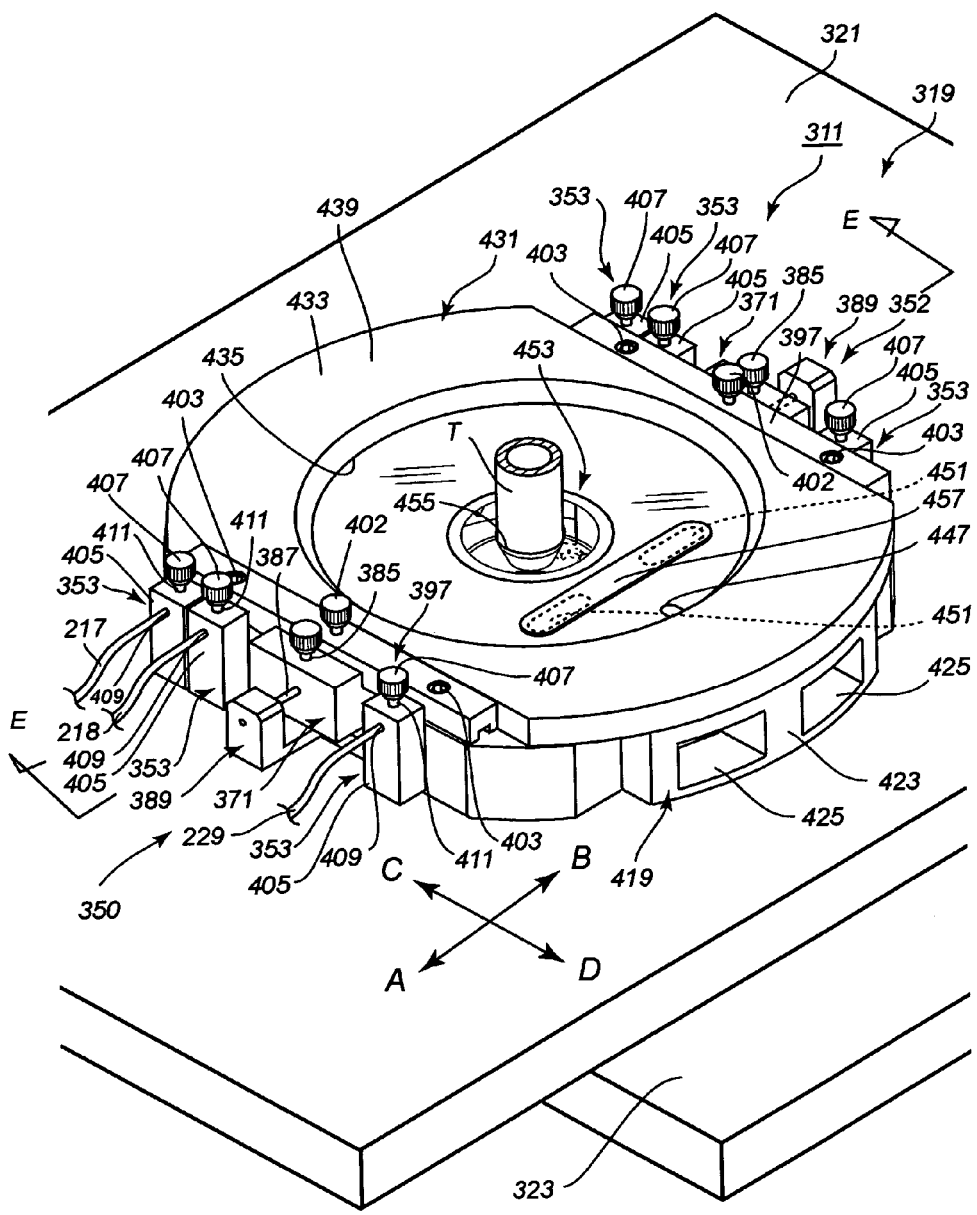
FIG. 13 is a perspective view showing the incubator in accordance with the second embodiment of the present invention placed on the stage of the microscope.

At first, the structure of the dish 220 used in the incubator 201 will be described with reference to FIGS. 10-12 as follows.

The dish 220 includes a circular, middle-depth dish body 221 of transparent plastic material, and a cover 223 therefor. The cover 223 includes at its upper surface a pair of half-pipe shaped protrusions 225 for connecting tubes. These protrusions 225 are disposed diametrically opposite with each other. Each protrusion 225 have a through hole 227 for connecting the tube formed therein. The through hole 227 has a L-shaped channel extending from the protrusion 225 as one open end to the lower surface of the cover 223 as the other open end (see FIG. 12). The one ends of the holes 227 are directed in the opposite directions respectively.

A tube 229 for delivering nutrient medium is inserted through the one hole 227 along the channel and protrude from the lower surface of the cover 223. A tube 231 for withdrawing nutrient medium is inserted through the other hole 227 along the channel and protrude from the lower surface of the cover 223.

The dish 220 may be formed of transparent glass.

An incubator assembly for observation by microscope includes the dish 220 and the incubator 201.

The water tank unit 203 includes a water tank 205, a container holder for holding the dish 220, a water-supplying pipe 213, a gas-supplying pipe 214, and tube holder 291.

The water tank 205 has a member comprising an annular bottom plate 205a and an outer peripheral wall 205b extending vertically from the outer edge of the bottom plate 205a, and a cylindrical inner peripheral wall 205d extending upwardly from the edge of an opening 205c formed through the bottom plate 205a. The outer area of the inner peripheral wall 205d makes an annular trough, which is referred hereinbelow as water reservoir 205e, and the inner area of the inner peripheral wall 205d makes a container-accommodating portion 205g.

A splash depressor 205i for preventing the water contained in the water reservoir 205e from rushing over the wall 205d is provided on an upper edge of the inner peripheral wall 205d.

The upper edge of the outer peripheral wall 205b is provided with four recesses 205f (see FIGS. 6 and 7) for threading tubes.

A pair of holder seats 206 is secured on the inner peripheral surface of the inner wall 205d at the diametrically opposite position. Each seat 206 has a crescent configuration and a shallow and broad groove 206a is provided on its upper surface. A tapped hole 206b is also provided through the groove 206a.

A pair of container holders 207 of a crank shaped cross sectional configuration is adapted to be mounted on each seat respectively. Each holder 207 has at its upper leg an oblong slot 207a therethrough and at the tip 207b of its lower leg a rectangular notch. The upper leg of the holder 207 is adapted to be accommodated slidably within the groove 206a of the seat 206, and secured fixedly thereto by a screw 208 threaded through the slot 207a into the hole 206b. The spacing between the tips 207b of the lower legs can be adjusted by loosening the screw, displacing the holder as desired, and then fastening it again.

Figure 6:
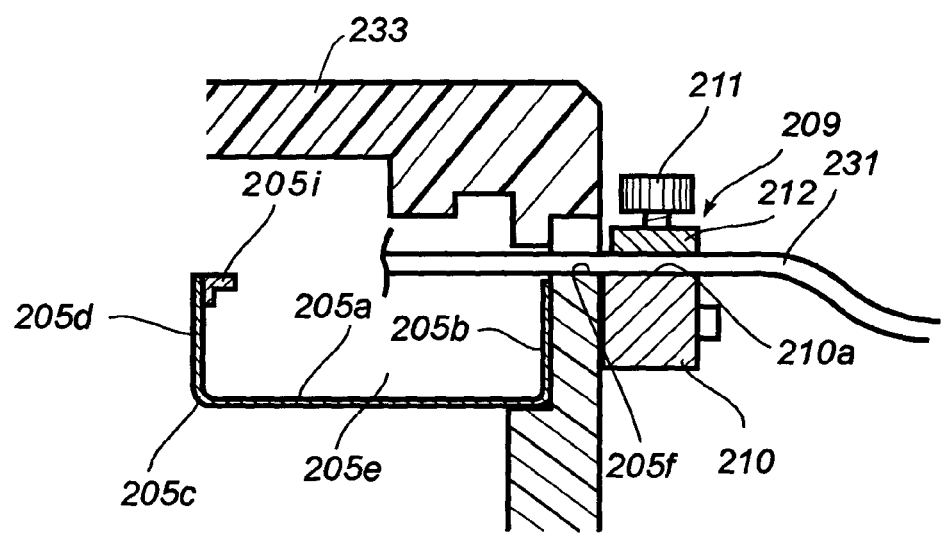
FIG. 6 is an enlarged cross sectional view taken along line C-C of FIG. 2.

A pair of tube holders 209 is provided on the outer peripheral surface of the wall 205b, the one for the tube 229 for delivering nutrient medium, and the other for the tube 231 for withdrawing nutrient medium. The holders 209 are disposed to be diametrically opposite with each other. Each tube holder 209 includes a base block 210 secured on the outer peripheral surface, and a keep plate 212 adapted to be urged on the upper surface of the base block 210 by means of a presser screw 211. The base block 210 has a holding recess 210a (see FIG. 6) formed therein. The construction of the tube holder 209 for the tube 231 for withdrawing nutrient medium as illustrated in FIG. 6 is same as that for the tube 229 for delivering nutrient medium.

The holding recess 210a of each tube holder 209 is adapted to be in line with each recess 205f formed through the wall 205b of the water tank 205.

The tubes 229 and 231 for delivering and withdrawing nutrient medium to the dish 220 are threaded through the recesses 205f and 210a, and secured thereto so as not to be withdrawn therefrom.

The tube 229 is connected to the tank for reserving nutrient medium through a filter (not shown) for removing contaminant such as germs or bacteria.

The means for supplying nutrient medium includes the tube 229 for delivering nutrient medium, the tube 231 for withdrawing nutrient medium, and the tank for reserving nutrient medium.

The nutrient medium may also be supplied by a syringe. For example, the nutrient medium contained in the syringe may be delivered by pushing a plunger to displace the medium through the tube 229 into the dish 220.

A pair of pipe holders 291 for supporting a water pipe 217 and a gas pipe 218 is also mounted on the outer peripheral surface of the wall 205b. These holders are juxtaposed in a predetermined distance from each other. Each pipe holder 291 includes a base block 293. The base block 293 has a horizontally extending lateral channel 295, which is formed through the wall 205b of the water tank 205 and leads to the recess 205f. The base block 293 has also a tapped hole 297 extending from the upper surface to the channel 295.

Figure 7:
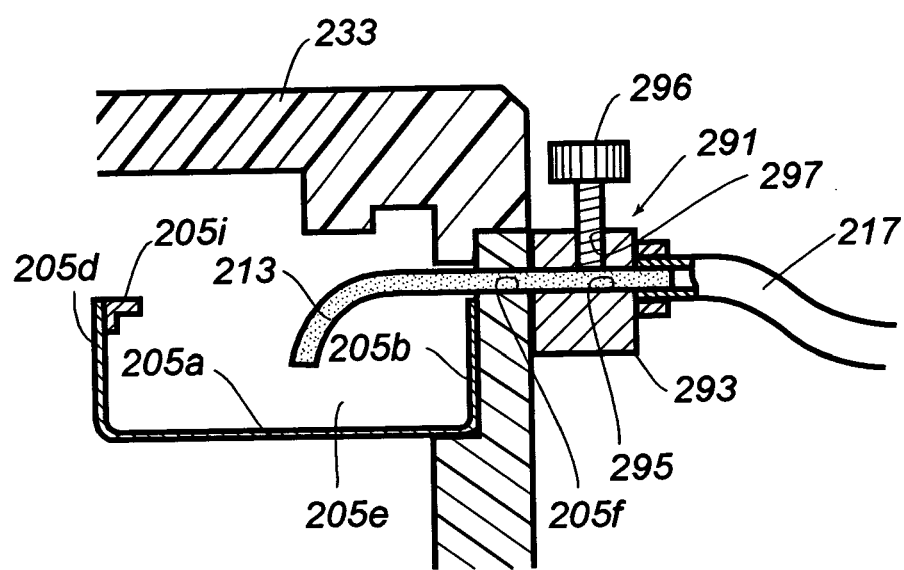
FIG. 7 is a partially cross sectional view taken substantially along line B-B of FIG. 3 wherein the off-the hook limiting lever is in its lock release position.

The water-supplying pipe 213 inserted through one channel 295 and one recess 205f is adapted to be secured by pressing the pipe by the tip of the presser screw 296 attached to the tapped hole 297 (see FIG. 7). Although the construction of the pipe holder 209 assigned for the water tube 217 is illustrated in FIG. 7, that assigned for the gas tube 218 can also be provided in the same construction.

The gas pipe 214 is also inserted through the other channel 295 and the other recess 205f, and secured by pressing the gas pipe by the tip of the presser screw 296 attached to the tapped hole 297 (see FIG. 7).

The water pipe 213 is curved downwardly at its tip portion protruding into the water tank 205 to dispose the tip opening 13a thereof below the upper edge of the wall 205d and above the bottom of the water reservoir 205e. The one end of the water supplying tube 217 is attached to the rear end of the water pipe 213 protruding from the channel 295 of the holder 209, and the other end of the tube 217 is attached to the infusion reservoir 216.

The water supplying means includes the water pipe 213, the infusion reservoir 216, and the water-supplying tube 217.

The gas pipe 214 is curved downwardly at its tip portion protruding into the water tank 205 to dispose the tip thereof near the bottom surface of the water reservoir 205e. One end of the gas-supplying tube 218 is attached to the rear end of the gas pipe 214 protruding from the channel 295 of the holder 209. The other end of the tube 218 is attached to a bomb for containing the carbon dioxide gas through a valve for preventing the reverse flow of water within the water reservoir 205e, a flow meter, and a control valve for adjusting the flow rate of the carbon dioxide gas.

The gas supplying means includes the gas pipe 214, the gas supplying tube 218, the control valve, and the bomb for containing the carbon dioxide gas.

The lid 233 includes a relatively thick annular lid plate 237 having a circular window 239 formed therein. A ring shaped protrusion 241 of the outer diameter smaller than that of the lid is formed on the lower surface of the lid plate 237. The window 239 is closed by a transparent heater plate 243 of glass attached to the lower surface of the lid plate 237.

The heater plate 243 includes a pair of glass plates 244 and 246, and a transparent conductive film formed on the lower surface of the upper glass 244 for converting electric energy into thermal energy. In order to control the electric current for delivering to the conductive film to adjust the thermal energy produced thereby and the temperature, a temperature sensor 257 is provided on the lower surface of the heater plate 243.

The heater plate 243 has a circular work hole 245 formed therein and offset relative to the periphery of the window 239. The heater plate 243 has a pair of tube holes 250 formed therein. When effecting culture operation without the cover 223, or exposing the dish 220, the tubes 229 and 231 are inserted through the tube holes 250, and the tip of these tubes are disposed within the dish 220 to exchange nutrient medium or culture media (B).

The work hole 245 is closed by a lid 249 and the tube holes 250 are closed by plugs 251.

The diameter of the lid 249 is slightly larger than that of the work hole 245. The work hole 245 is closed by disposing the lid 249 so as to surround the edge of the opening of the work hole 245 by an adhesive ring 253 of silicone rubber attached to the outer peripheral portion of the lower surface of the lid 249. The lid 249 also has formed therein a smaller work hole 255, which is closed by the plug 251.

The plug 251 is a disk shaped silicone rubber slightly larger than the tube holes 250 and the work hole 255.

A signal wire extending from the temperature sensor 257 is connected to the temperature controlling means (not shown).

The heater plate 259 includes a ring shaped frame 261 of plastic. The outer diameter of the frame 261 is slightly smaller than the inner diameter of the water tank unit 203. A ring shaped annular protrusion 263 extends downwardly from the lower surface of the frame 261. The plate is further provided with an inner flange 265 extending from the inner peripheral surface of the frame near the upper surface thereof. The outer diameter of the protrusion 263 can be set to the diameter of the tool-fixing hole 269 of the stage 267 of the microscope.

A top plate 271 of transparent glass is rest on the inner flange 265 of the frame 261. An upper plate 275 is provided below the top plate 271 with interposing a thin spacing 272 therebetween. The top plate 271 is somewhat thicker than the spacing 272. The top plate 271 also has a circular hole 273 at the central portion thereof.

A laminate including the upper and lower plates 275 and 277 of anodized aluminum material, and a heater 279 of nichrome material interposed between plates is disposed below the inner flange 265 of the frame 261. The upper plate 275 is adhered on the lower surface of the inner flange 265, and thus the laminate including the upper and lower plates 275 and 277, and the heater 279 are mounted on the inner flange 265 so as to depend therefrom. The upper and lower plates 275 and 277 are of annular configuration and have been alumite-treated.

The upper and lower plates 275 and 277 have holes 275a and 277a of relatively larger diameter than that of the hole 273 of the top plate 271.

The light-transmitting channel is defined by the holes 275a, 277a, the hole 273 of the top plate 271, the window provided through the lid plate 237, and the opening 205c defined through the bottom plate 205a.

Although not shown in the attached drawings, the frame 261 is also provided with a spacing through which cords extending from the temperature controller (not shown) to the heater 279 are laid.

Each of Fixtures 281, 283 has a thick sheet body of rectangular cross section larger in its height than the width and of the same radius of curvature as that of the outer peripheral surface of the water tank 205. The bottom surface of the fixture 281, 283 is provided with a both sides adhesive tape. Each of the fixtures 181, 283 has a pair of horizontally extending tap holes 284 through which a pair of presser screws 285 are to be threaded.

The concrete structure of a jig assembly for securing the fixtures 281, 283 on the desired position on the stage 267 of microscope will now be described.

The jig assembly includes a centering member 290 and an outer jig member 294. The centering member 290 has an annular disk shaped body of the substantially same size as that of the dish 220, and it have a circular hole 292 formed at the center thereof. The diameter of the hole 292 is the same as that of the hole 275a of the upper plate 275. The outer jig member 294 has a ring shaped body to be fit snugly around the outer periphery of the water tank 205. The members 294 also have along the outer periphery thereof, a pair of diametrically opposite recesses 298 for accommodating the fixtures 281, 283. The width of the portion of the member 294 at which the recess 298 is formed is around 5 mm.

The incubator assembly for observation by microscope includes the jig assembly for securing the fixtures and the incubator 201.

The method for using the incubator 201 will now be described.

Figure 8:
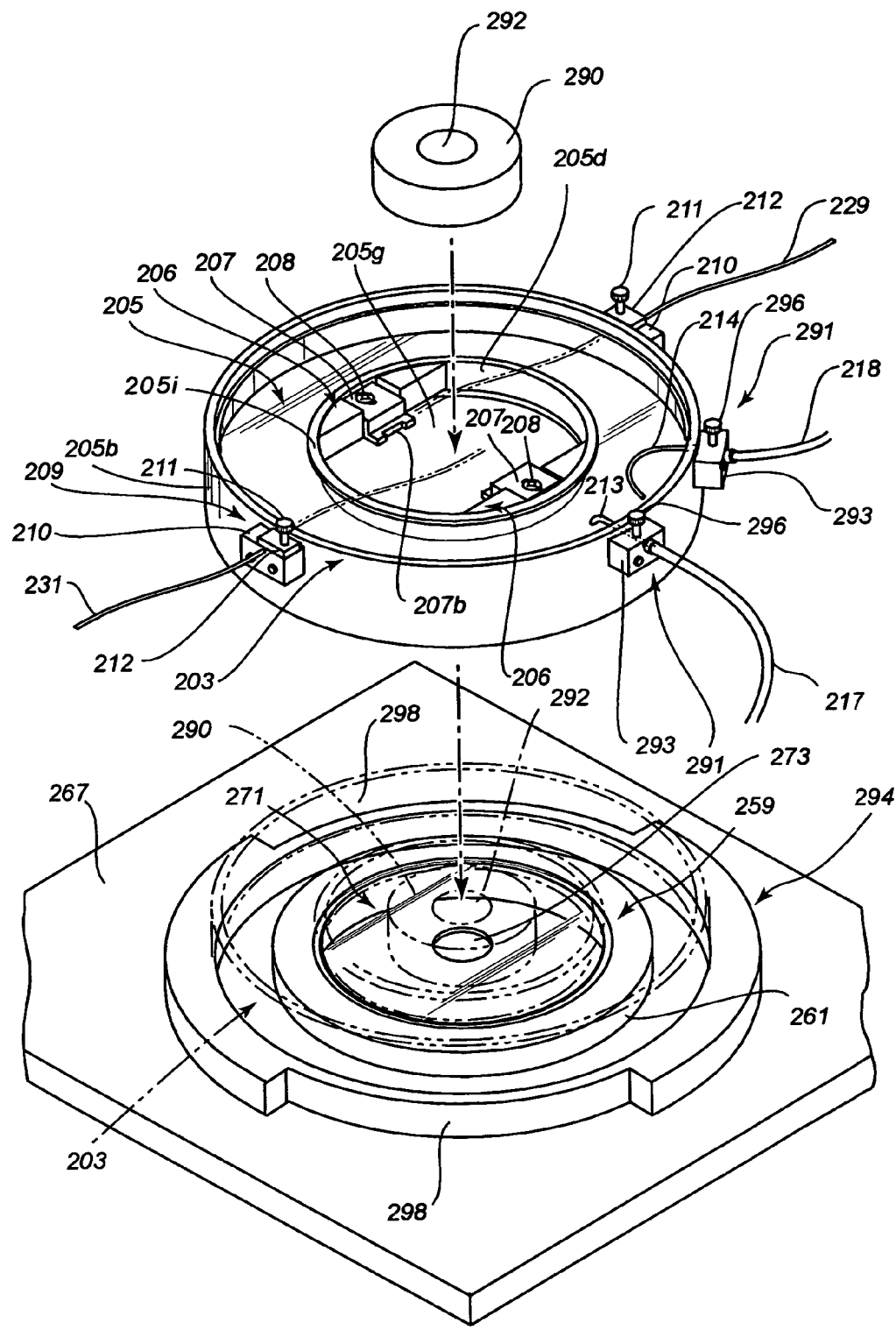
FIG. 8 is an exploded perspective view showing the operation to be effected to secure the fixtures using a jig assembly for securing the fixtures.
Figure 9:
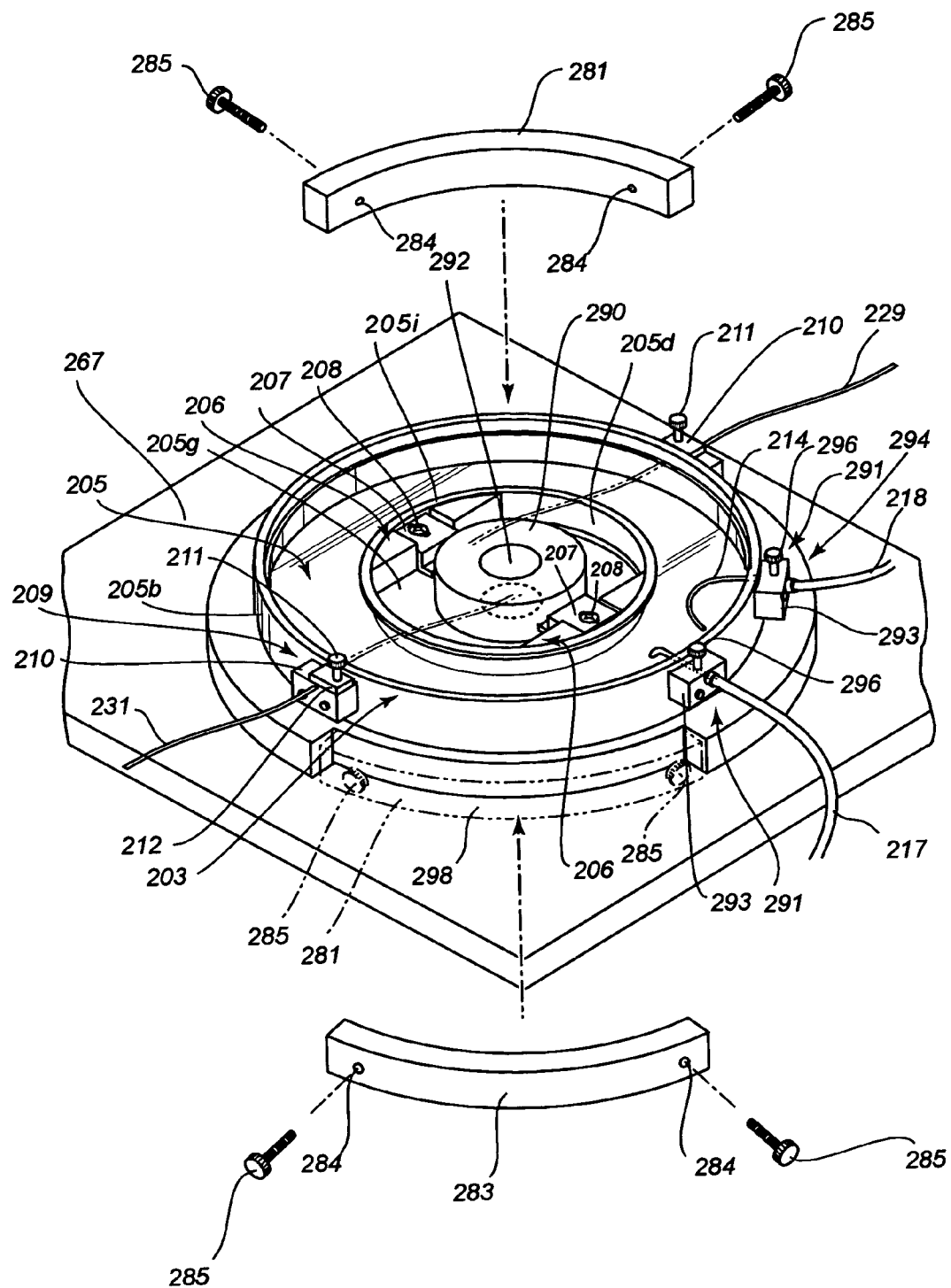
FIG. 9 is an exploded perspective view showing the operation to be effected to secure the fixtures using a jig assembly for securing the fixtures.

At first, the operation for securing the fixture 281 and 283 to the stage 267 of the microscope by using the jig assembly will be described with reference to FIGS. 8 and 9.

The heater plate 259 is placed on the stage 267 of the microscope with inserting the ring shaped annular protrusion 263 of the frame 261 into the tool of the stage 267. The outer jig member 294 is then placed on the stage 267 to the position of the frame 261. Subsequently, the water tank 205 is placed over the heater plate 259 to fit the outer peripheral portion of the tank 205 into the outer jig member 294.

Subsequently, the centering member 290 is placed on the top plate 271 at the center of the container-accommodating portion 205g; the container holders 207 are displaced to contact the tips 207b with the outer peripheral surface of the centering member 290. Then the screws 208 are tightened to secure the holder 207 to keep the centering member 290. The water tank 205 is then adjusted to coincide the hole 292 of the centering member 290 with the hole 275a of the upper plate 275.

The outer jig member 294 is then indexed or rotated to bring the recess 298 of the member 294 to the position in which the fixtures 281 and 283 are to be secured.

The presser screws 285 are threaded horizontally into the fixtures 281 and 283 so as not to protrude the tips beyond the surface of the fixtures 281 and 283 facing to the water tank 205. Thus positioned fixtures 281 and 283 are fit to the recess 298 and secured on the stage 267 by means of the adhesive tape, and then the centering member 290 is removed.

After the fixtures 281 and 283 are secured on the stage 267, the water tank 205 is lifted from the stage 267 to remove the outer jig member 294, and then the tank 205 is again brought down on the stage 267 as it were. Thus, the fixtures 281 and 283 are spaced by 5 mm from the outer peripheral surface of the tank 205. Then the presser screws 208 are turned to extend the tips from the fixtures 281 and 283 to the outer peripheral surface of the tank 205 to position the water tank unit 203 securely on the stage 267. If it is requested to change an observed portion, the position of the unit can be adjusted within the range allowed by the clearance between the fixtures 281, 283, and the tank 205, which is 5 mm to the fixtures 281, 283 respectively.

The operation for securing the dish will now be described.

After the screws 208 are loosened to free the holder 207, the dish 220 is placed on the top plate 271 within the container-accommodating portion 205g of the water tank 205. Then the holders 207 are moved toward the dish 220 to urge the tips 207b against the outer peripheral surface of the dish body 221, and then the screws 208 extending through the oblong slot 207a into the hole 206b are fastened to hold the dish 220 by the holders 207. The tubes 229 and 231 for delivering and withdrawing nutrient medium extend from the dish 220. These tubes are then threaded through the recesses 205f and 210a and secured to the base block 210 by means of keep plate 212.

The specimen such as cells to be observed is preliminary contained in the dish 220 with some nutrient medium.

The method for supplying water and carbon dioxide gas into the incubator 201 will now be described.

The water contained in the infusion reservoir 216 hanged on any hanger above the water tank unit 203 is delivered by gravity through the water supplying tube 217 and the water pipe 213 to the water reservoir 205e within the unit 203. The reservoir 205e is thus filled with water. Upon reaching the level of the water in the reservoir 205e to the level of the tip opening 213a of the pipe 213, the supplying of the water is stopped spontaneously. The lowering of the level of the water through evaporation is compensated by the water contained in the infusion reservoir 216. Thus the level of the water in the reservoir 205e is maintained in a predetermined level, and the amount (W) of water contained in the reservoir 205e is kept constant. The water may be delivered by means of syringe with reference to the amount of water contained in the reservoir 205e or periodically.

In the incubator 201, the water pipe 213 is seen through the heater plate 243 of transparent glass from outside of the incubator 201. This is because the window 239 is formed to be circular. In this connection, the level of water contained in the reservoir 205e can be easily ascertained at a glance.

The operation of the incubator 201 in accordance with the first embodiment will now be described.

When heating the water contained in the reservoir 205e to generate water vapor, the heater plates 243 and 259 are energized under the control of the controller (not shown) to heat the dish 220 and the water tank 205 to evaporate the water in the reservoir 205e. The incubation space 235 is thus filled with water vapor and the dish 220 is exposed thereto. The relative humidity of the incubation space 235 can be kept in the range between 90 and 95% and the temperature in dependence on the amount of heat energy provided through the heater plates 243 and 259. The humidity within the dish 220 can be maintained in the uniform humidity, since the dish 220 is positioned in the center of the incubation space 235 surrounded by the reservoir 205e.

The concentration of carbon dioxide gas within the incubation space 235 can be kept in 5%. This can be done by delivering the carbon dioxide gas of 5% through the control valve and the gas tube 218 into the space 235. Although the concentration of carbon dioxide gas within the space 235 is leaked out from the space through the clearance between the water tank 205 of the incubator 201 and the lid 233, the gas is continuously delivered. Thus the space 235 is maintained at the 5% gas concentration.

The concentration of carbon dioxide gas within the space 235 can also be kept constant by any other methods. When it is necessary to keep the gas concentration within the space 235 substantially constant, carbon dioxide gas of much higher concentration can be delivered intermittently into the space 235 based on information from a sensor for detecting the gas concentration within the incubation space 235.

The gas to be delivered into the space 235 is not limited to carbon dioxide gas, and it may be nitrogen gas or oxygen gas.

As can be seen from the above, the incubation of the specimen (e.g. germs or cells) can be effected under the predetermined temperature, humidity and concentration of carbon dioxide gas, and change of nutrient medium is done without removing the lid 233 or the cover 223 of the dish 220. In other words, the amount of nutrient medium in the dish 220 is kept constant by withdrawing the deprived medium (B) through the tube 231 and delivering flesh medium through the tube 229 of the amount substantially identical with the withdrawn medium. Thus, the incubator 201 and the dish 220 allow the circulation incubation with changing nutrient medium.

The tubes 229 and 231 can be inserted and withdrawn easily through the aperture 227 so that the amount of nutrient medium (B) can be controlled by adjusting the height (the distance from the bottom surface of the dish 220) of the tip opening 23 1. In other words, the amount of the medium (B) can be increased by rising the level of the medium (B) and by increasing the height of the tip opening 231 of the tube 231. Whereas the amount of the medium (B) can be decreased by lowering the level of the medium (B) by decreasing the height of the tip opening 23 1 of the tube 231.

When observing the specimen within the dish 220, the ray of light irradiated from the condenser (C) pass through the hole 273 of the top plate 271, the hole 275a of the upper plate 275, and the hole 277a of the lower plate 277, and is incident into the objective lens (T). Thus, variation of the specimen with time within the dish 220 can be observed and recorded while incubating the specimen.

The heater plate 259 is spaced from the water tank unit 203 so that the variation of the weight of the unit 203 due to the variation of the amount of the medium contained in the reservoir 205e does not bring any effects on the heater plate 259. Thus, the distance between the dish 220 and the objective lens (T) is maintained constant to prevent the observed image from unclear.

The clearness of the observed image can also be enhanced by spacing the top plate 271 on which the dish 220 is placed above the upper plate 275 of the heater plate 259. The influence to be applied on the dish 220 by thermal expansion or deformation of the top plate 275 due to the temperature variation of the heater plate 259 is smaller than the case in which the dish 220 is placed directly on the upper plate 275. This is because the coefficient of expansion of the glass material forming the top plate 271 is lower than that of the aluminum material forming the heater plate 259. Thus, the unclearness due to the variation of the distance between the specimen and the objective lens (T) can be avoided more effectively.

The laminate comprising the upper plate 275, the lower plate 277, and the heater 279 deforms downwardly upon heated since the laminate is attached to the inner flange 265 to depend therefrom. The effect on the dish 220 through the deformation of the laminate including the upper plate 275 can be reduced to the minimum, and the unclearness of the image to be observed can be avoided.

The deformation of the upper plate 275 does not influence the dish 220. This is because there is the spacing 272 between the top plate 271 and the upper plate 275. Thus, the effect for avoiding the unclearness due to the variation of the distance between the specimen and the objective lens (T) can be enhanced further.

The observation through microscope with interposing any oil or water between the bottom surface of the dish 220 and the objective lens (T) may effected, because the incubator 201 for observation by microscope 201 includes the hole 273, the hole 275a, and the hole 277a.

In addition, the incubator 201, upon removing the water tank unit 203, can be used to observe the specimen on a slide glass or the like with heating it.

An incubator 311 in accordance with a second embodiment of the present invention will now be described with reference to FIGS. 13-26. The incubator 311 is that to be used in erecting microscope.

The same component or components of the incubator 311 as that of the incubator 201 of the first embodiment are designated by the same reference numerals, and the descriptions thereof will be omitted.

The incubator 311 includes a water tank unit 347 to which a dish 313 is adapted to be placed removably therefrom, a lid 431 for covering the upper surface of the unit 347, and a heater plate 317 for heating the unit 347 and the dish 313. The incubator 311 is adapted to be mounted on the driving stage 319 including a pair of superposed stage plates 321 and 323.

The upper plate 321 is adapted to be displaced horizontally in the left to right direction (referred hereinbelow to as A-B direction), and the lower plate 323 is adapted to be displaced horizontally in the front to rear direction (referred hereinbelow to as C-D direction). Thus, the incubator 311 can be displaced in both of the A-B direction and the C-D direction. The upper plate 321 is also provided with a circular tool-fitting hole 269.

The construction of the heater plate 317 will be described.

The frame designated by the reference numeral 325 is of aluminum alloy, and the outer diameter of which is slightly smaller than the inner diameter of the water tank unit 347. The frame includes an inner flange 327 extending inwardly from the inner surface thereof. The inner flange 327 supports on its upper surface the outer periphery of the lower surface of a top plate 328 of glass material. The place 330 for supporting the container of the specimen to which the dish 313 is to be placed is defined on the central portion of the upper surface of the top plate 328.

A transparent heater plate 329 of glass laminate structure is secured on the lower surface of the inner flange 327. The heater plate 329 includes a pair of transparent glass plates (i.e. upper glass plate 333 and lower glass plate 331) and a transparent conductive film 335 of an ITO film formed on the upper surface of the lower glass plate 331. The transparent conductive film 335 is adapted to be energized through a pair of spaced terminals (or electrodes) provided thereon.

There is spacing between the upper surface of the transparent heater plate 329 and the lower surface of the top plate 328.

The frame is provided its outer peripheral surface with an outer flange 337 and a stepped portion 339, i.e. the frame has two kinds of shoulders different in their diameter, so that it is possible to fit the heater plate 317 into two kinds of tool fitting holes different in their diameter.

Figure 14:
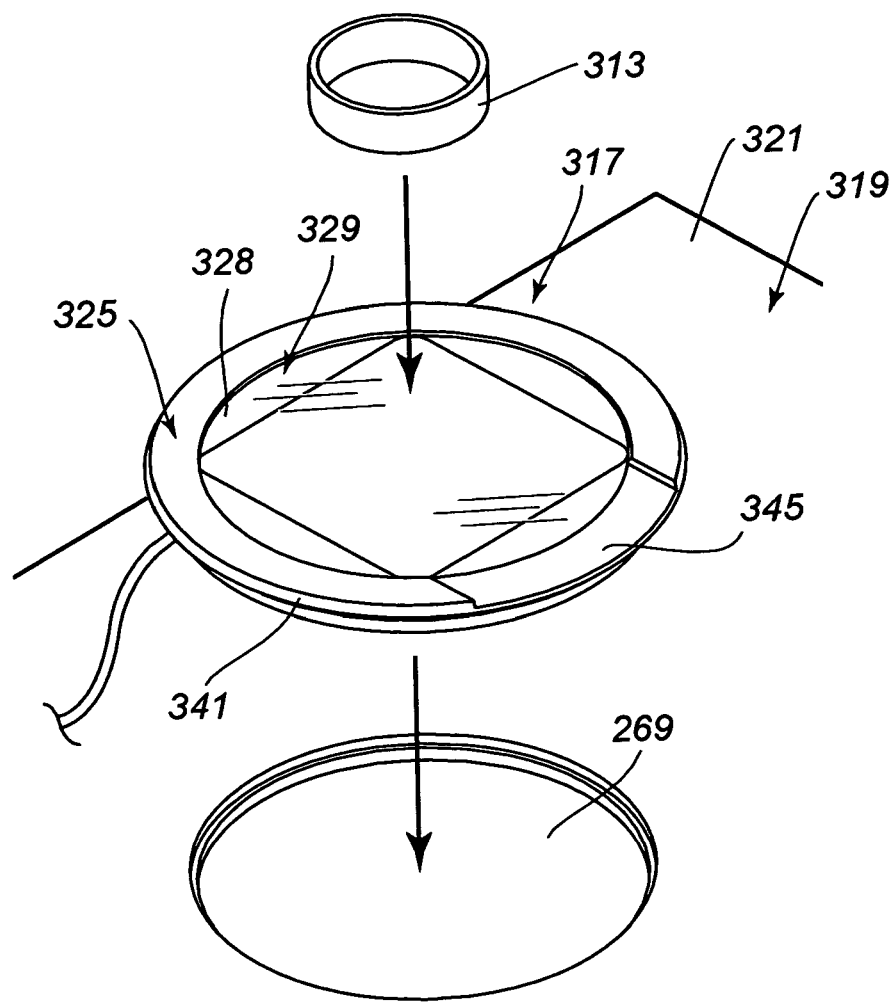
FIG. 14 is a perspective view showing the operation to be carried out for fixing the incubator in accordance with the second embodiment of the present invention on the stage of the microscope.
Figure 14:
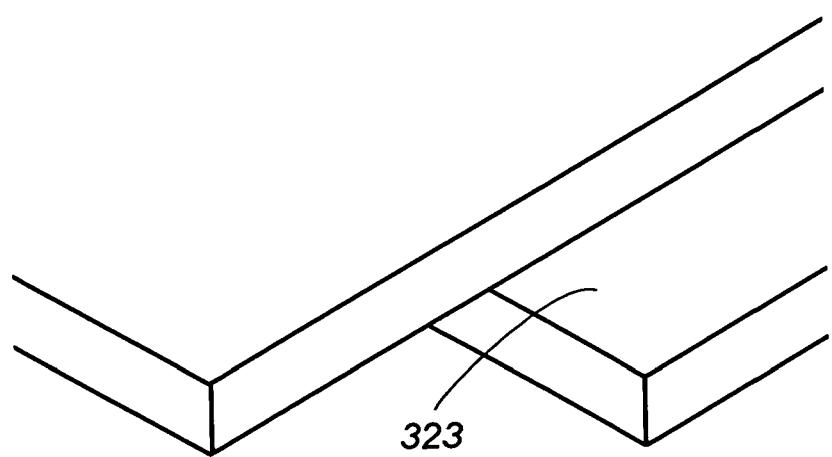
Figure 15:
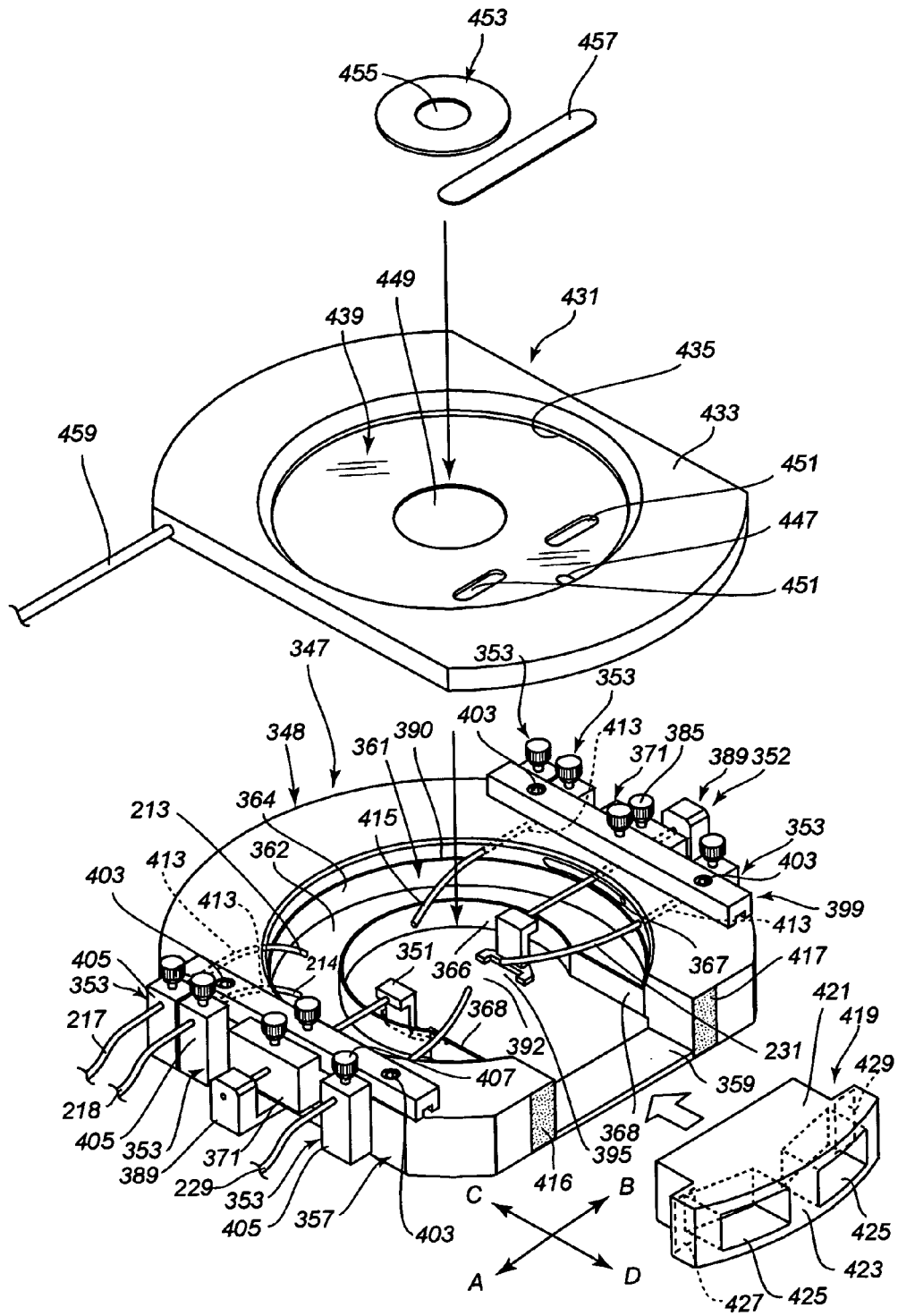
FIG. 15 is a perspective view showing the operation to be carried out for fixing the incubator in accordance with the second embodiment of the present invention on the stage of the microscope.
Figure 16:
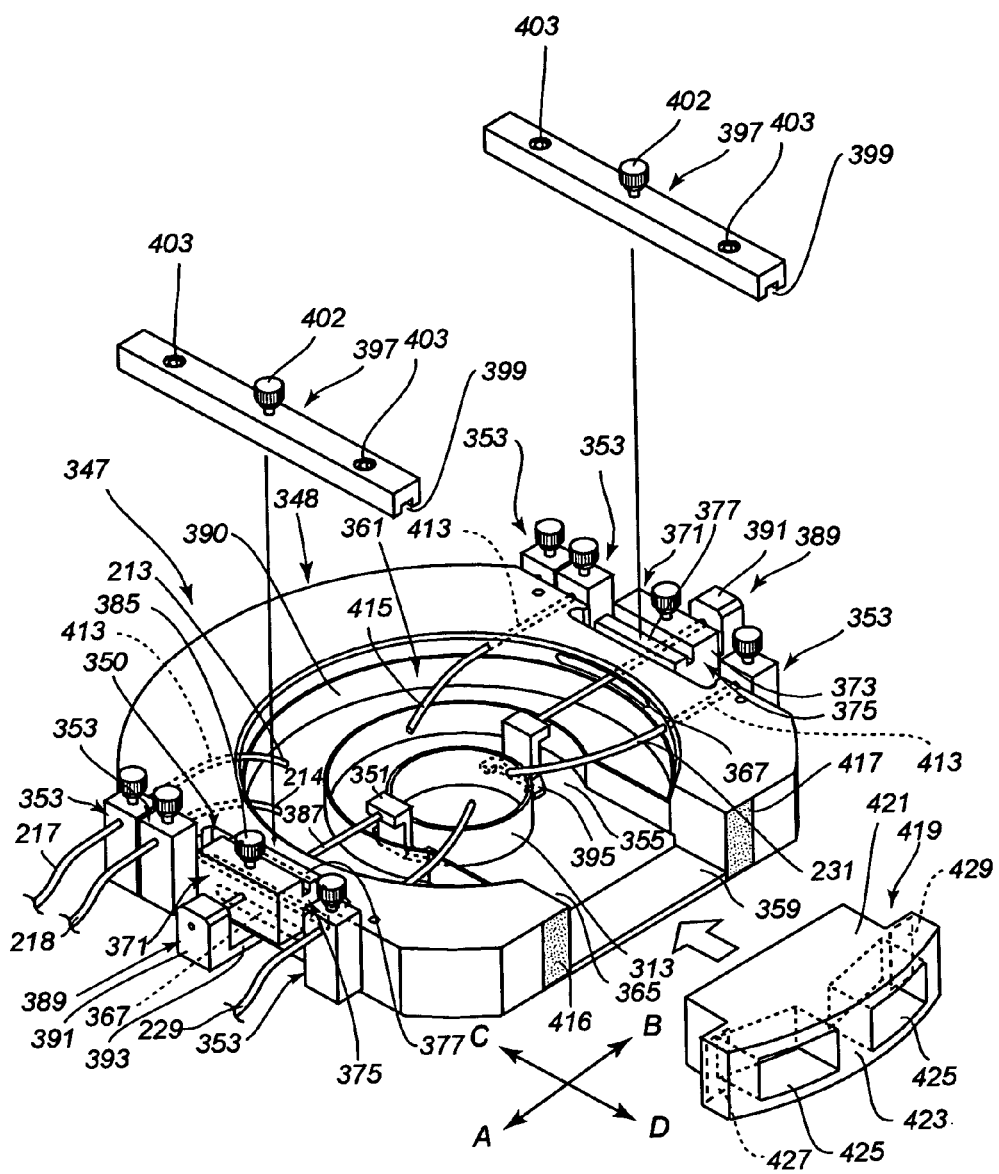
FIG. 16 is an exploded perspective view showing a water tank unit of the incubator in accordance with the second embodiment of the present invention.
Figure 17:
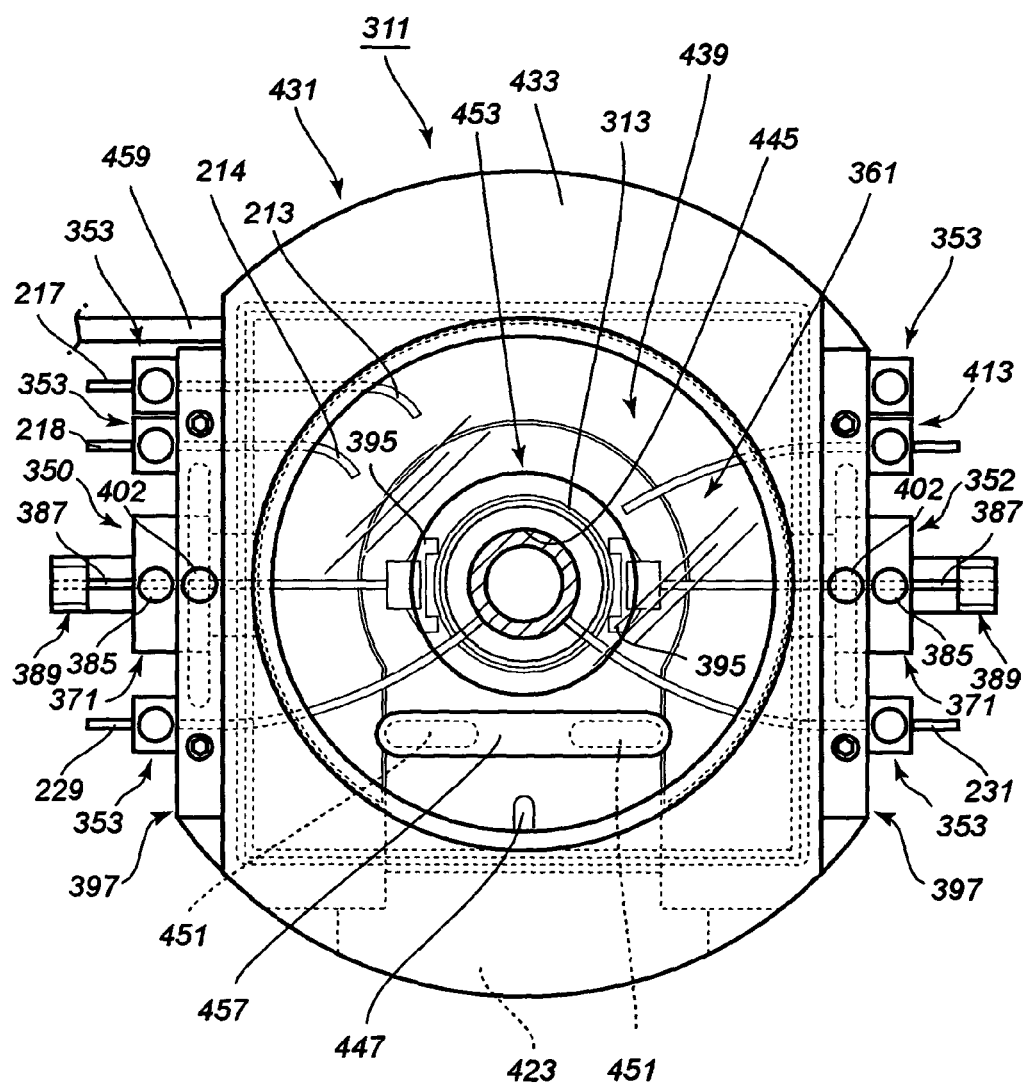
FIG. 17 is a plan view showing the incubator for observation by microscope in accordance with the second embodiment.

As can be seen from FIG. 14, a portion 345 of the upper surface of the frame 325 is removed to the height of the upper surface of the top plate 328 to which the container of the specimen to be placed.

The structure of the water tank unit 347 will now be described.

The water tank unit 347 includes a unit body 348, a water tank 361, a container holder 351 for holding the dish 313, a water supplying tube 213, a gas supplying tube 214, and tube holder 353.

The unit body 348 is of plastic material and has an opening 355 extending vertically through the central portion thereof. An entrance opening 359 is provided through the peripheral wall of the unit body 348. The entrance opening 359 extends from the upper surface of the body to nearly the bottom surface thereof. Thus, a thin-sheet shaped bridging portion is left on the entrance opening 359.

The water tank 361 is a "C-shaped" shallow container because of the presence of the discontinuity 365. The water tank 361 includes a bottom plate 362, an inner peripheral wall 366, an outer peripheral wall 364, and closure plates 368 extending between the inner and outer walls. A water tank reservoir 390 is defined between the bottom plate 362a, the inner peripheral wall 366, the outer peripheral wall 364, and closure plates 368.

The water tank 361 is contained within the opening 355. The outer periphery of the bottom of the tank 361 is supported on the shoulder formed on the inner peripheral surface of the unit body 348 with contacting the outer peripheral wall 364 with the inner peripheral surface of the unit body 348. The area defined within the inner peripheral wall 366 is a container-accommodating portion 392.

Figure 18:
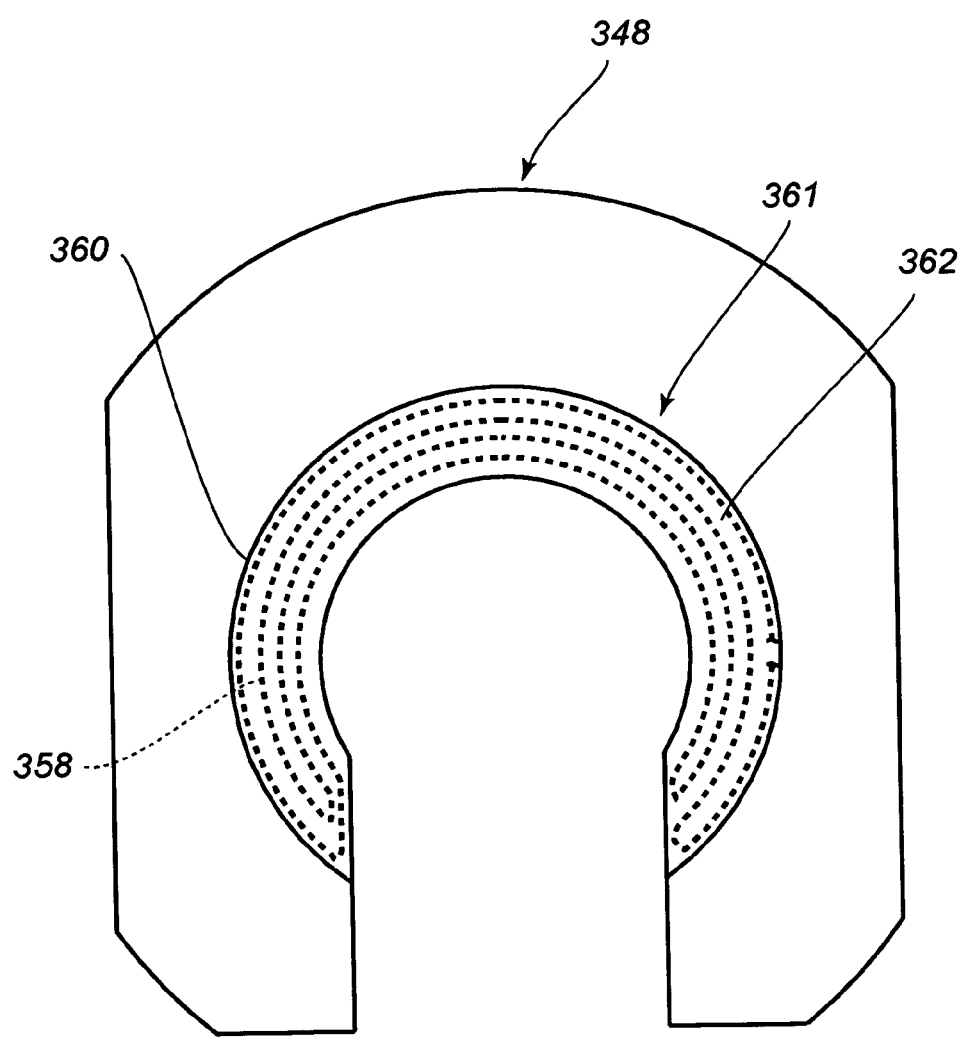
FIG. 18 is a bottom plan view showing the water tank unit of the incubator for observation by microscope in accordance with the second embodiment.

As shown in FIG. 18, a water tank heater 358 of an insulated nichrome wire is provided under the tank 361. The heater 358 is covered with a heater cover 360 of plastic material.

A means for displacing the specimen container will now be described.

The means comprising a pair of symmetrical left and right displacing mechanisms 350 and 352, so that the structure of the left mechanism will only be described and that for the right one will be omitted.

Figure 20:
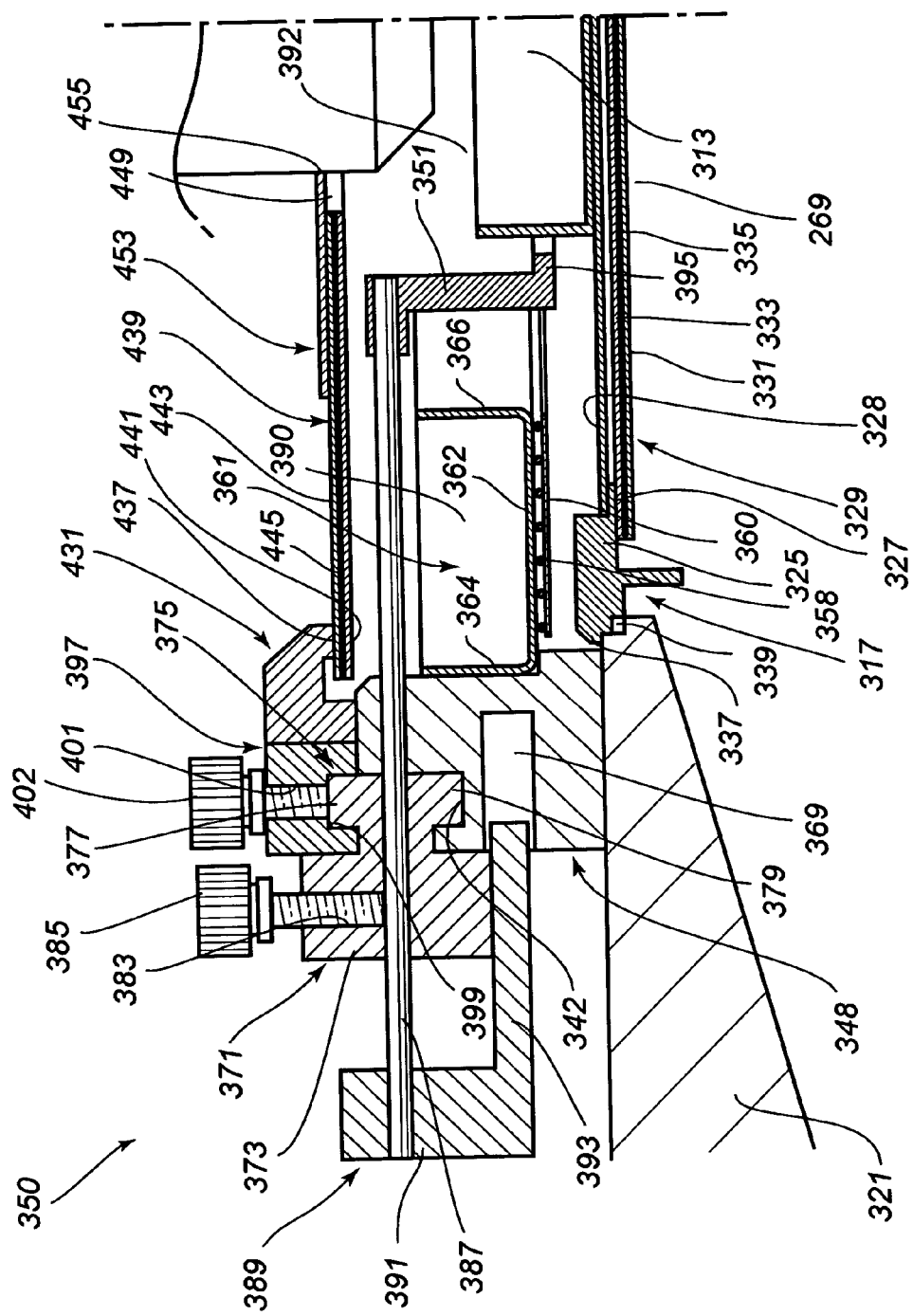
FIG. 20 is an enlarged view taken partially from FIG. 19.

The upper and left portion of the peripheral wall 357 is removed to form a shoulder 340 and then the upper surface of thus formed shoulder is formed with a guiding recess 342 extending in the C-D direction (see FIG. 20). The portion of the peripheral wall 357 extending upwardly from the shoulder is provided with a long, through hole 367 extending laterally. The portion of the peripheral wall 357 extending downwardly from the shoulder is provided with an accommodating recess 369 extending in the A-B direction.

Figure 19:
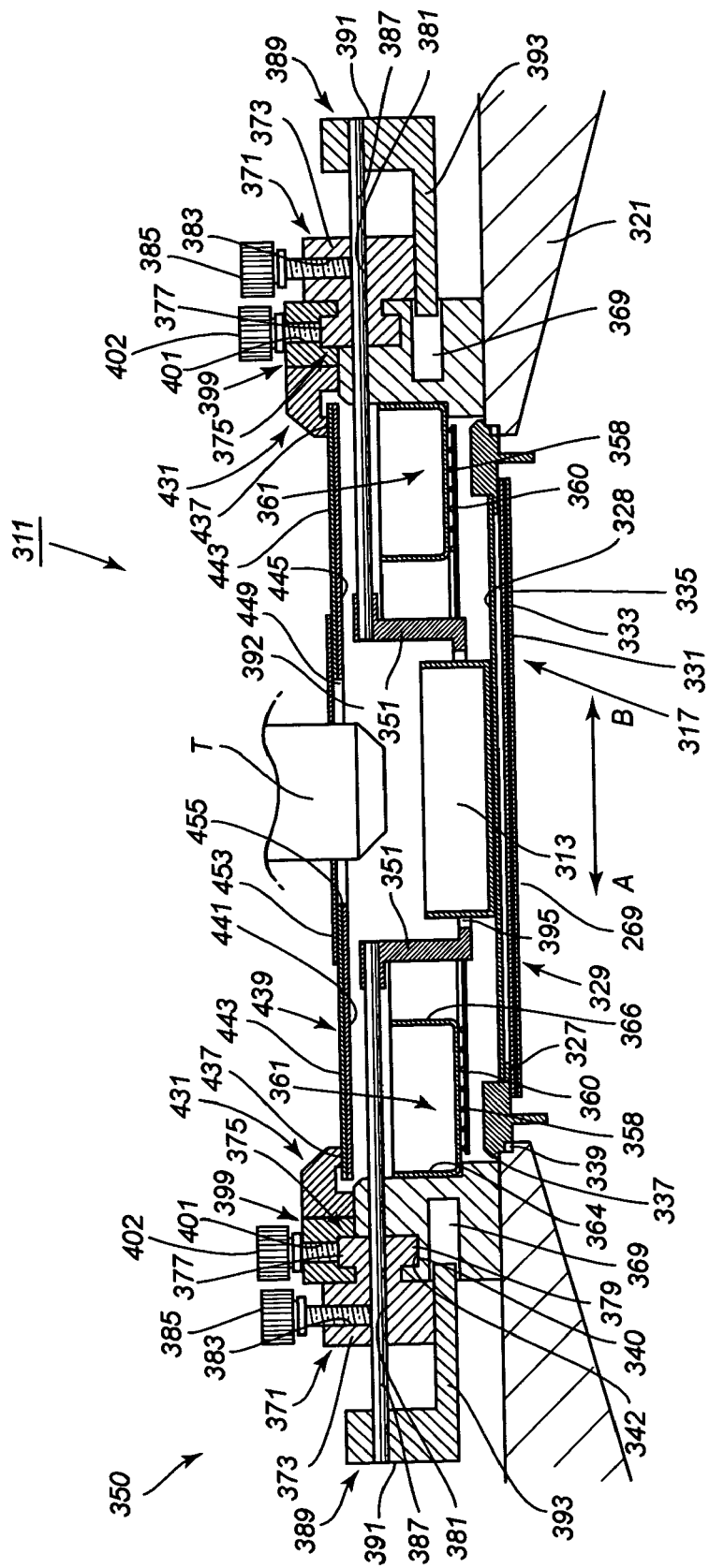
FIG. 19 is a cross sectional view taken substantially along line E-E of FIG. 13.

A slider 371 includes a slider body 373 and mounting potion 375 (see FIG. 19). The mounting potion 375 includes an upwardly extending portion 377 and a downwardly extending portion 379. The slider 371 has therein a through hole 381 for passing the shaft 387, and a tapped hole 383 extending from the upper surface of the slider body 383 to the through hole 381 to which the presser screw 385 is to be screwed.

The shaft 387 is connected to the vertical portion 391 of the "L-shaped" control member 389. The horizontally extending portion 393 of the control member 389 is inserted into the accommodating recess 369. The container holder 351 is connected at the tip of the shaft 387. The container holder 351 has a crank shaped cross sectional configuration. The holder 351 has at the tip 395 of its lower leg a rectangular recess.

There is a presser member 397 having on the lower surface, a guiding recess 399 extending in the C-D direction. The presser member 397 has a tapped hole 401 leading to the recess 399 to which a presser screw 402 is to be attached.

The downwardly extending portion 379 of the slider 371 is adapted to be fit within the guiding recess 342 formed on the shoulder 340. The presser member 397 is secured on the upper surface of the peripheral wall 357 by means of attaching screws 403 with fitting the guiding recess 399 with the upwardly extending portion 377. The slider 371 can be displaced in the C-D direction through the cooperation of the upwardly and downwardly extending portions 377, 379 and the recesses 342, 399. The holders 351 are positioned on a container-accommodating portion 392 surrounded by the inner peripheral wall 366.

The means for displacing the specimen container is constructed as described above.

The water tank unit 347 includes six tube holders 353 disposed three by three on each of left and right sides thereof. Each tube holder 353 includes a base block 405 secured on the outer peripheral wall and a presser screw 407. The base block 405 has a through hole 409 extending in the A-B direction, and a tapped hole 411 extending from the upper surface thereof to the hole 409. A presser screw 407 is to be attached to the tapped hole 411. The unit body 348 has also therein six holes 413 for threading tubing. The two of the six holes are further provided with pipes 213 and 214 for delivering water and gas. These pipes are bent at their tip portion towards the water tank reservoir 399. Those to be attached to the holes 409 of the base block 405 are a water tube 217, a gas tube 218, a nutrient medium delivering tube 229, a nutrient medium withdrawing tube, 231 and a temperature sensor 415. The water tube 217 is connected to the pipe 213, and the gas tube 218 is connected to the pipe 214. The pipes 217 and 218 and the temperature sensor 415 extends from the holes 214 provided through the unit body 348 to the container-accommodating portion 392. The remaining one tube holder 353 is a reserve part.

The front face of the unit body 348 is provided with a pair of magnet sheets 416 and 417.

A side closure member 419 includes an insert portion 421 and a handle portion 423 larger in its width than that of the insert portion 421. Thus formed shoulder of the handle portion 423 is provided with a metal thin sheet 427 and 429 of iron. The handle portion 423 is provided with a pair of rectangular recesses 425.

The structure of a lid 431 will now be described.

A lid plate 433 is of substantially annular shape, and both sides thereof is cut off in parallel. In other words, the sides of the plate 433 in the A-B direction are planer, and the sides in the C-D direction are circular (see FIG. 15). The size of the plate 433 in the A-B direction is slightly larger than the distance between the presser members 397. A circular window 435 is provided through the lid plate 433. The lower surface of the inner portion of the plate 433 is removed to form an annular shoulder including at the lower side of the inner peripheral portion thereof an annular protrusion 437. A heater plate 439 of transparent glass is attached to the lower surface of the protrusion 437. The upper surface of the heater plate 439 forms a portion of the lid 431.

A transparent heater plate 439 of glass laminate structure includes a pair of transparent glass plates 441 and 443 and a transparent conductive film 445 of an ITO film formed on the upper surface of the lower glass plate 441. The transparent conductive film 445 can convert electric energy to generate heat energy. The electric energy to be delivered to the film 445 of the heater 439 is adapted to be controlled based on information obtained from temperature sensor 447 provided on the heater 439. Thus, the temperature may be controlled within the predetermined range.

A circular aperture 449 is formed through the central portion of the heater plate 439. The heater plate 439 has formed therein a pair of oblong slots 451 larger in its dimension in the A-B direction through which any operation will be carried out to the specimen.

A cover plate 453 is made of thin transparent glass adapted to be disposed on the heater plate 439 for covering the aperture 449. The cover plate 453 has a hole 455 for accepting the lens of the microscope. The pair of slots 451 is covered with a closure member 457.

The lid 431 is provided with cords 459 for supplying electric energy to the film 445 and for transmitting the signal from the temperature sensor 447 to the controller (not shown).

Figure 21:
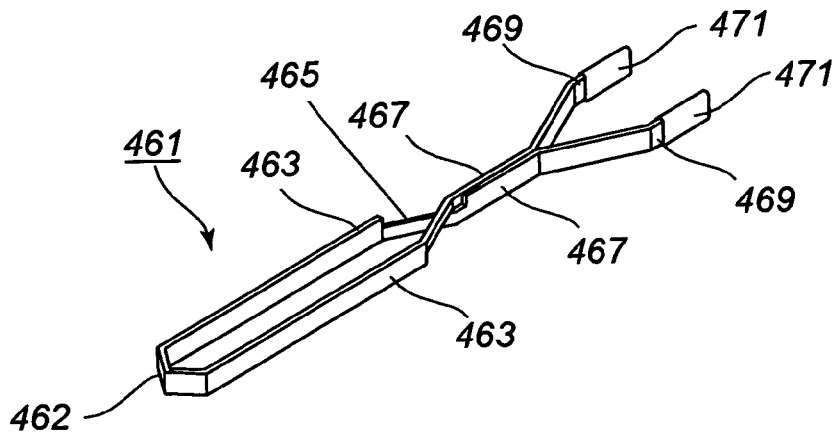
FIG. 21 is a perspective view showing the structure and the method for using the dish tongs.
Figure 22:
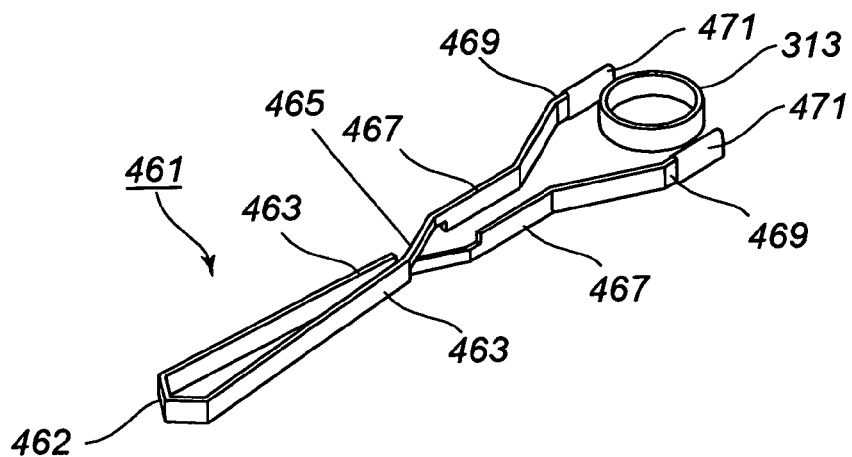
FIG. 22 is a perspective view showing the structure and the method for using the dish tongs.
Figure 23:
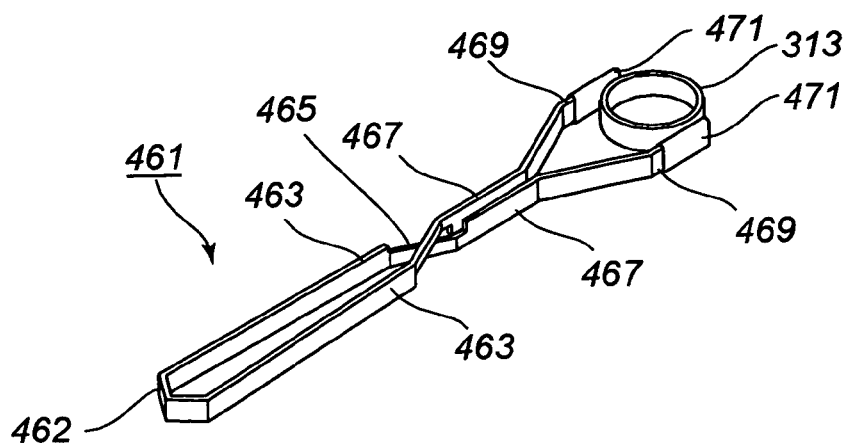
FIG. 23 is a perspective view showing the structure and the method for using the dish tongs.
Figure 24:
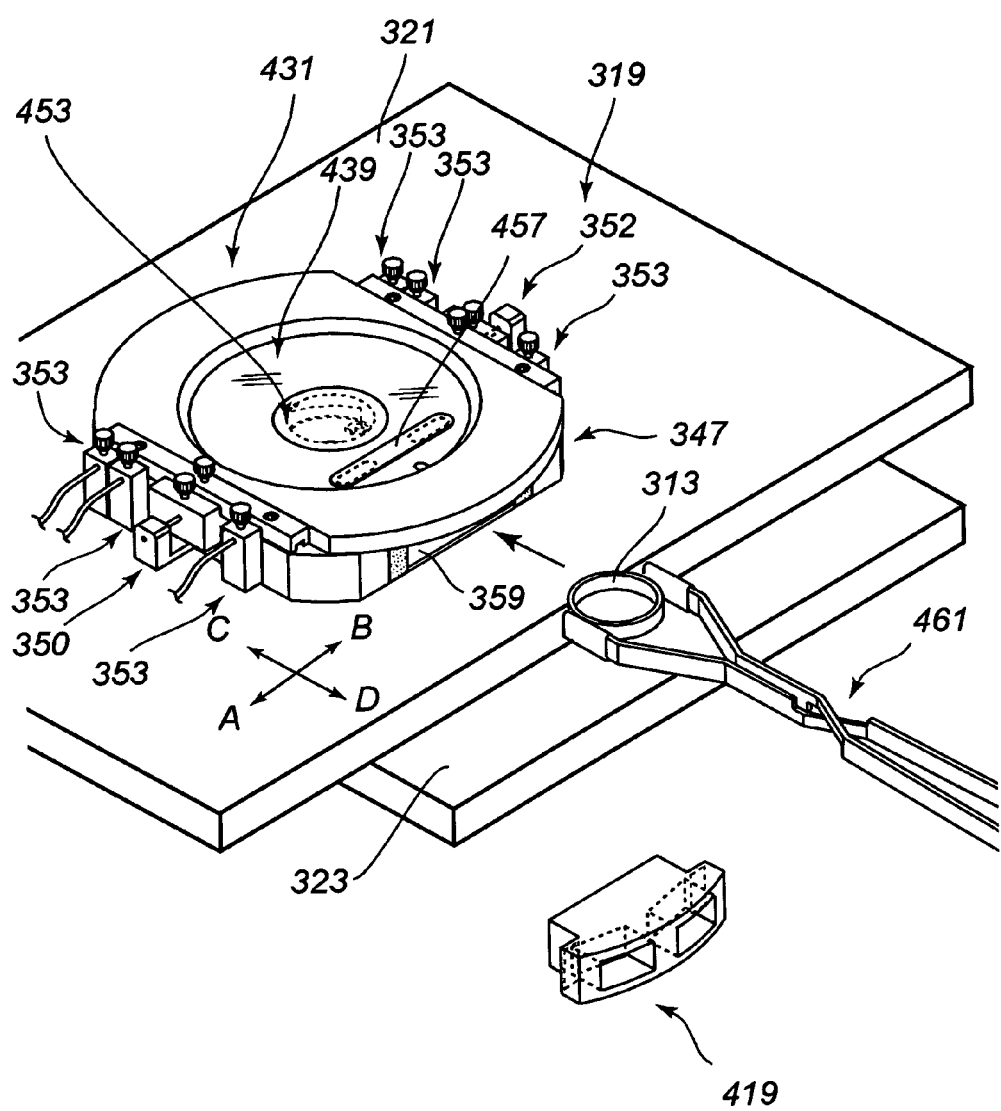
FIG. 24 is an exploded perspective view showing the operation to be effected to put the dish by means of dish tongs into and out of the incubator in accordance with the second embodiment of the present invention.
Figure 25:
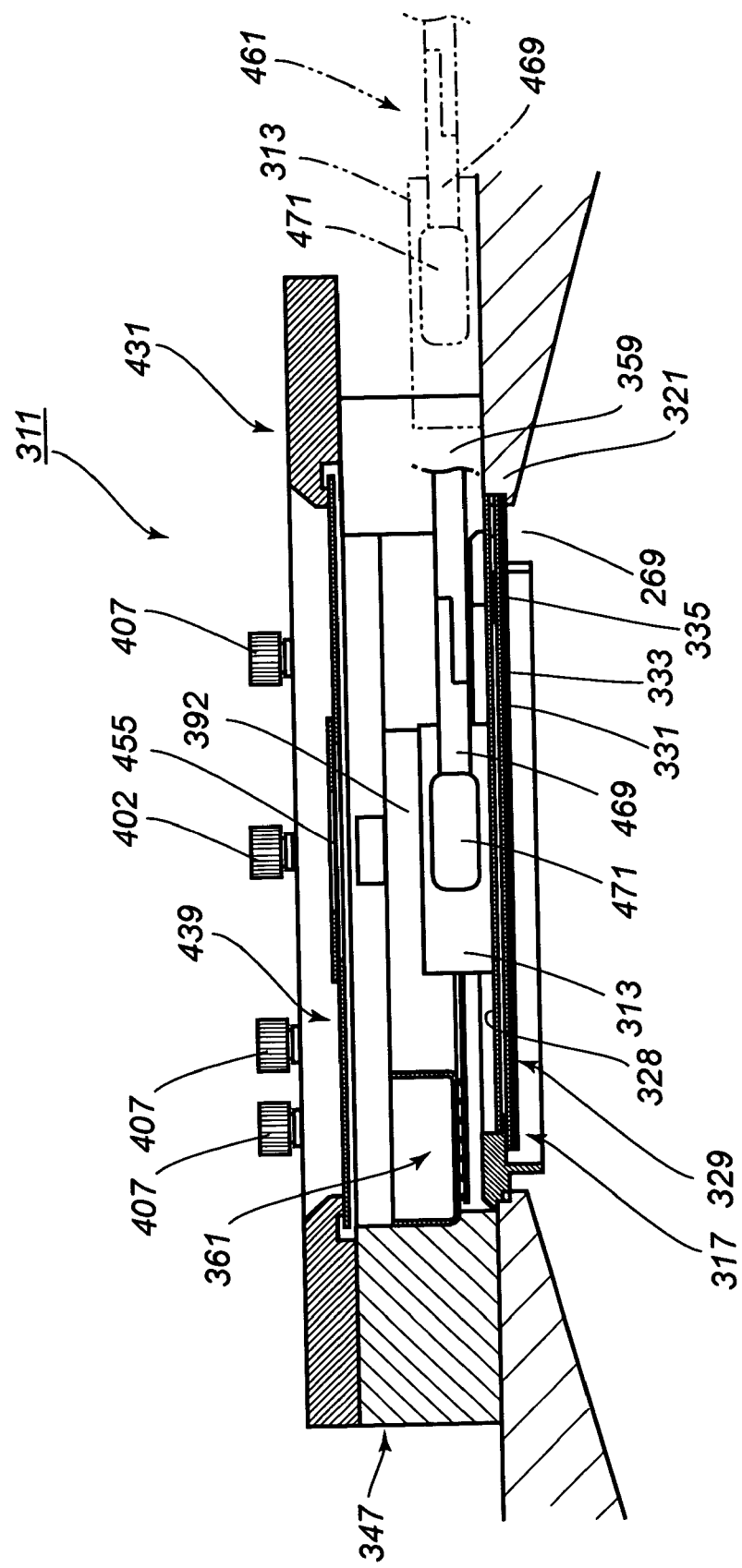
FIG. 25 is a cross sectional view showing the operation to be effected to put the dish by means of dish tongs into and out of the incubator in accordance with the second embodiment of the present invention.

The structure and the operation of a dish tongs 461 will now be described with reference to FIGS. 21-23.

The tongs 461 of elastically deformable stainless steel has a pair of arms 463 connected at the rear ends or proximal ends thereof. These arms are crossed with each other at the crossing portion 465 provided through the middle portion of these arms. The arms further include a pair of urging portions 467 to be urged against each other by the force generated by the elastic deformation of the material of the tongs. The portions of the arms extending distally from the urging portions are bent away from each other and then bent back to form a pair of parallel pinching portions 469. A pair of slip-proof caps 471 of synthetic rubber is fit on the pinching portions 469. The minimum spacing between the pinching portions 469 can be kept constant by the abutment of the portions 467.

The tongs 461 and the incubator 311 for observation by microscope form an incubator assembly for observation by microscope.

The method for using the incubator 311 of the second embodiment and the mode of operation of the incubator will now be described.

At first, the manipulation effected to fit the incubator 311 on the driving stage 319 will be described.

The heater plate 317 is placed on the tool fitting hole 269 formed through the upper plate 321 of the driving stage 319 as shown in FIG. 14. In this condition, the upper surface of the top plate 328 of the heater plate 317, a portion 345 of the upper surface of the frame 325 removed to the height of the upper surface of the top plate 328, and the upper surface of the upper plate 321, are all placed in the same height, i. e. flush with each other. The dish 313 to be placed on the container-accommodating portion 392 of the water tank unit 347 is placed on the place 330 for supporting the container of the specimen.

The water tank unit 347 is then mounted on the upper plate 321 to align the container-accommodating portion 392 with the place 330 for supporting the container of the specimen, and the lid 431 is then placed on the unit 347 to cover the upper opening of the unit 347. The aperture 449 of the heater plate 439 is covered with the cover plate 453, the pair of oblong slots 451 are closed by the closure member 457, and the entrance 359 is closed by the side closure member 419. The entrance 359 can surely be closed by the side closure member 419 through attracting the iron plates 427 and 429 onto the magnet sheets 416 and 417 provided on the unit body 348.

The incubator 311 is mounted on the driving stage 319 as described above. The space defined by the unit 347 and the lid 431 makes an incubation space 320.

The controller is then energized.

The water tank reservoir 390 is adapted to be filled with water supplied from the water tank through the water tube 217 and the water pipe 213. The incubation space 320 is filled with carbon dioxide gas from the bomb for containing carbon dioxide gas through the gas tube 218 and the gas pipe 214.

The transparent conductive film 335 of the transparent heater plate 329 of the heater plate 317 is energized through a pair of spaced terminals provided thereon to generate heat energy. The water tank heater 358 is energized to generate heat energy to heat the water tank 361 directly. The transparent conductive film 335 of the heater plate 439 of the lid 431 is energized through a pair of spaced terminals provided thereon to generate heat energy. The heater plate 329 and the water tank heater 358 are energized based on information detected by the temperature sensor 415, and the heater plate 439 is energized based on information detected by the temperature sensor 447.

The water contained in the water tank reservoir 390 is vaporized by heat energy provided by the heaters 329, 358, and 439. More particularly, sufficient amount of vapor can be generated quickly by heating the water in the water tank reservoir 390 directly by means of the water tank heater 358. The specimen within the dish 313 can be heated uniformly by heating whole of the bottom of the dish 313 through the transparent heater plate 329 of the heater plate 317. The heater plate 439 of the lid 431 can be prevented from fogging.

After the incubation condition in the incubation space 320 such as the temperature, the humidity, and the concentration of carbon dioxide gas had reached the predetermined value, the side closure member 419 is removed to open the entrance. Then the dish 313 is held by the tongs 461 to bring it through the entrance 359 into the container-accommodating portion 392, and placed in the place 330 for supporting the container of the specimen (see FIG. 25). The objectives such as cells are contained in the dish 313.

Depending on the kind of the specimen to be incubated, the dish 313 may be placed within the container-accommodating portion 392 without the lid or before fitting the lid.

If squeezing the potion of the tongs 461 proximal to the crossing portion 465 of the arms 463, the pinching portions 469 are displaced away from each other. Then the dish 313 is placed between the portions 469 and removing the squeezing force to hold the dish between the portions 469 by the force generated by elastic deformation of the material of the tongs. The dish 313 is carried by the tongs through the entrance 359 into the place 330.

Then the entrance 359 is closed by fitting the side closure member 419 into the unit body 348. The fitting aperture of the side closure member 419 can be made by holding the handle portion 423 by fingers of the operator. The pair of rectangular recesses 425 of the handle will prevent the fingers from slipped out therefrom.

The dish 313 can be removed from the container-accommodating portion 392 by means of the tongs 461 through the entrance 359. As can be seen from the above, putting in and out of the dish 313 from the portion 392 can be made without affecting the balance among the incubation conditions in the space 320 such as temperature, the humidity, and the concentration of carbon dioxide gas, i. e. without affecting the incubation of the specimen.

The upper surface of the top plate 328 of the heater plate 317, a portion 345 of the upper surface of the frame 325 removed to the height of the upper surface of the top plate 328, and the upper surface of the upper plate 321 are all placed in the same height as described above. Thus there are no steps. In this connection, putting in and out of the dish 313 from the portion 392 can be made smoothly without any obstruction.

Subsequently, the presser screws 385 of the pair of left and right displacing mechanisms 350 and 352 of the means for displacing the specimen container are loosened to enable the shaft 387 to be displaced. Then the shaft 387 is displaced in the A-B direction by displacing the vertical portion 391 of the control member 389 to push the dish 313 through the holder 351 to shift the dish in the A-B direction to the desired position. Then the screws are tightened to hold the shaft 387 by the tip thereof to secure the position of the holder 351. In the conditions, the dish 313 is interposed between the rectangular recesses provided at the tips 395 of the holders 351.

The lid 431 can be shifted along the presser members 397 in the C direction to align the oblong slots 451 with the dish 313. The closure member 457 is removed to guide the tubes 229 and 231 for nutrient medium into the dish 313.

The specimen such as cells contained in the dish 313 can be observed by the objective lens (T) inserted into the hole 455 provided through the cover 453.

When it is intended to change the area of the specimen in the dish 313 to which the objective lens (T) is to be directed, it is only necessary to shift the driving stage 319 in the A-B direction and/or in the C-D direction as desired. It is not necessary to withdraw the objective lens (T) from the hole 455 provided through the cover 453. Upon shifted the stage 319, the incubator 311 is also shifted together with the stage 319 except for the cover 453. In other words, upon shifted the stage 319, the heater plate 439 shifts relative to the cover 453 since the objective lens (T) abut against the inner peripheral edge of the hole 455 of the cover 453. Thus, the area to be observed can be changed by shifting the driving stage 319 within the range determined by the aperture 449 without removing the cover 453 from the aperture 449. Thus, the balance between the incubation conditions in the space 320 such as temperature, the humidity, and the concentration of carbon dioxide gas can be kept as it was since the aperture 449 is kept close by the cover 453.

Figure 26:
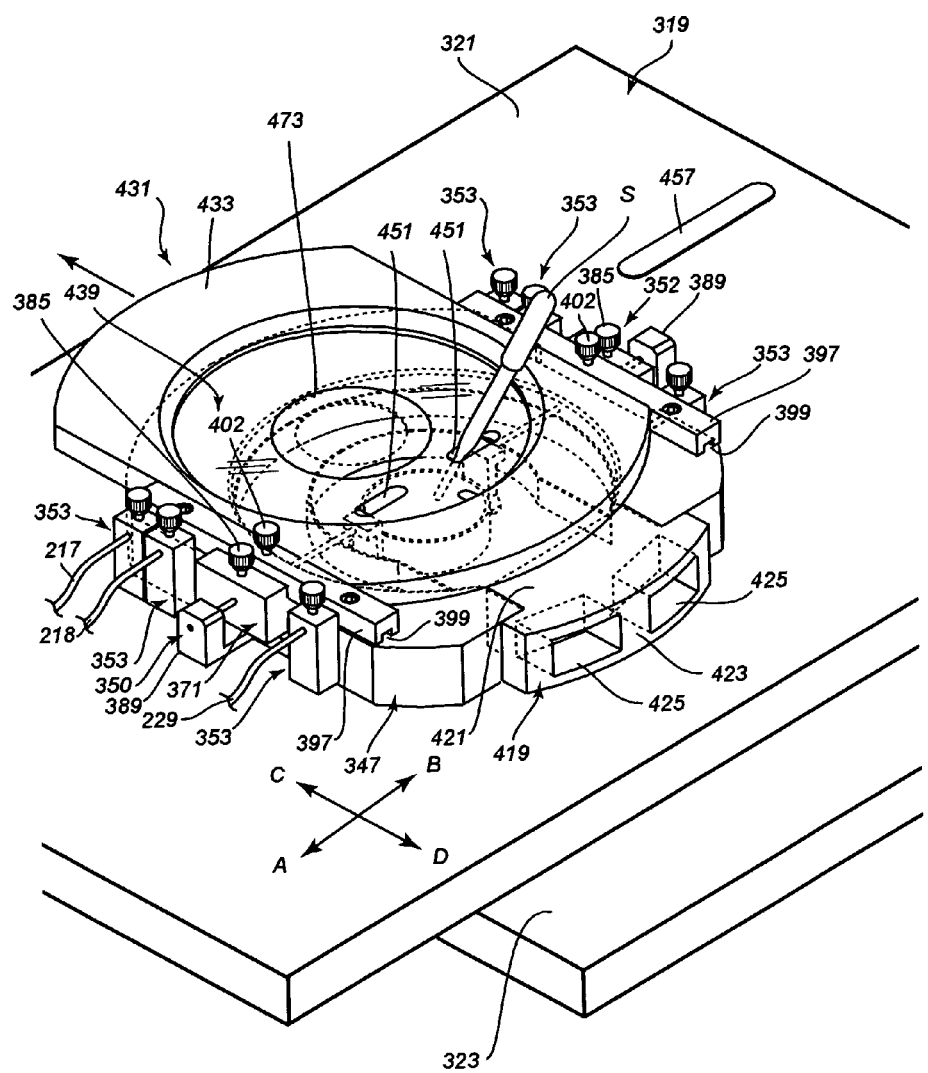
FIG. 26 is a perspective view showing the operation to be carried out to the specimen in the dish disposed within the incubator in accordance with the second embodiment of the present invention.

When drugs or chemicals are intended to be added to the specimen in the dish 313, it is necessary to retract the objective lens (T) to withdraw it from the hole 455 as shown in FIG. 26, and the cover 453 is replaced by the closure cover 473 without any holes to close the aperture 449. The lid 431 is shifted along the presser members 397 in the C direction to align the oblong slots 451 with the dish 313, and drugs or chemicals are added into the dish 313 by the syringe (S) inserted through the slots 451. Thus, any operation can be made to the specimen without spoiling the condition within the incubation space 320.

Figure 27:
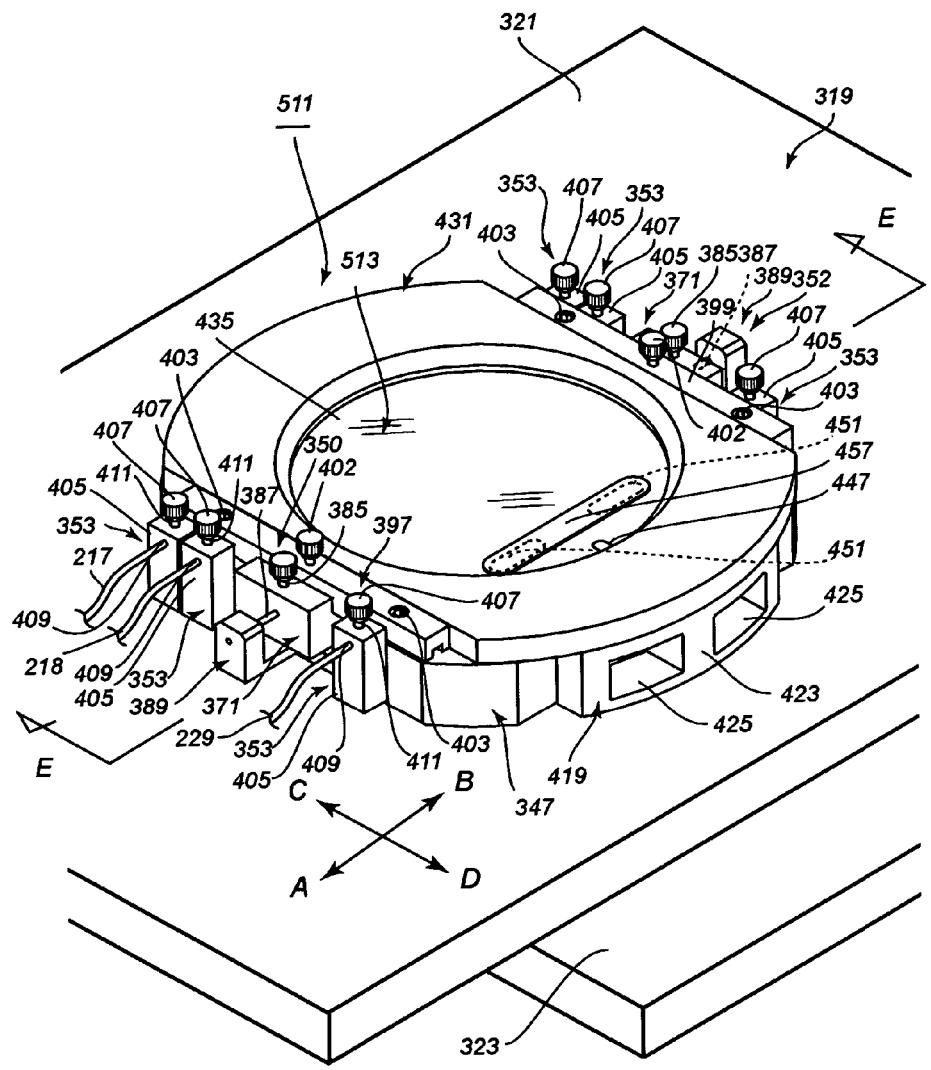
FIG. 27 is a perspective view showing the incubator in accordance with the third embodiment of the present invention placed on the stage of the microscope.
Figure 28:
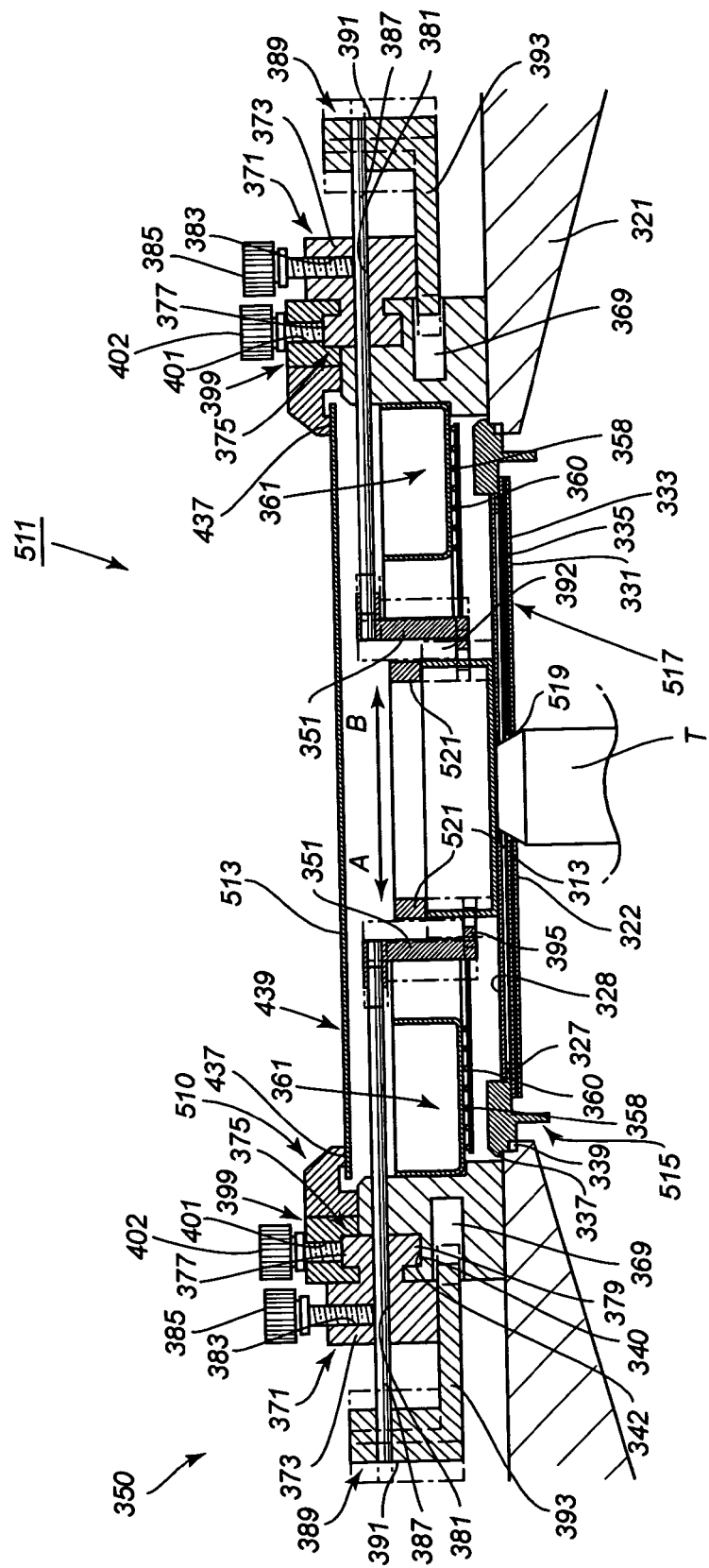
FIG. 28 is a cross sectional view taken substantially along line E-E of FIG. 27.
Figure 29:
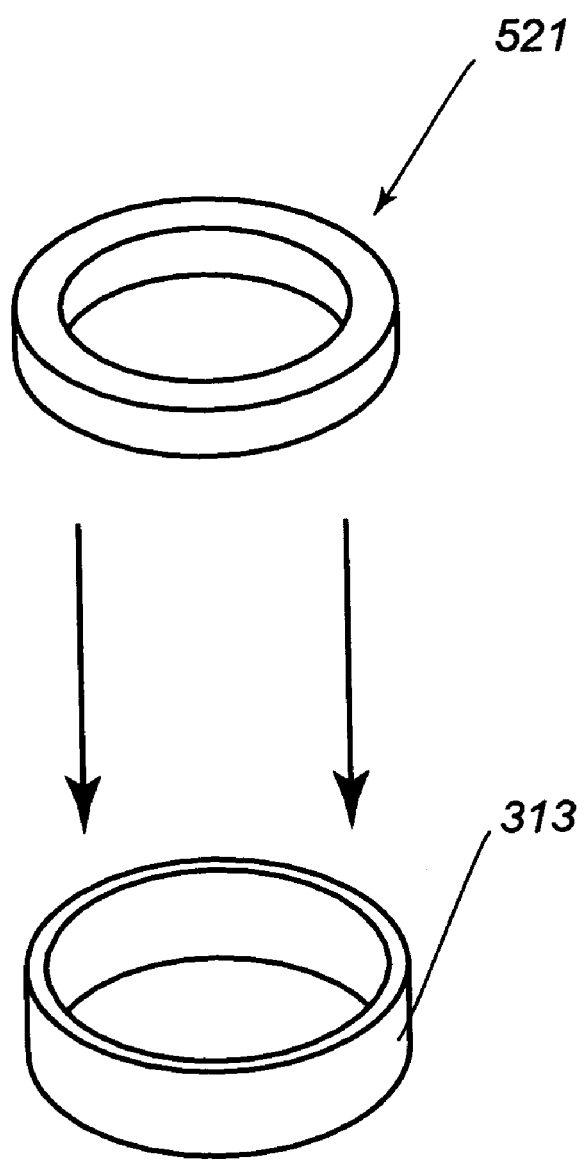
FIG. 29 is a perspective view showing the dish and the weight to be placed on the dish when any oil or water is interposed between the bottom surface of the dish and the objective lens.

An incubator 511 for observation by microscope in accordance with the third embodiment of the present invention will now be described with reference to FIGS. 27-29. The incubator 511 is that to be used in the inverted microscope.

The same component or components of the incubator 511 as that of the incubator 311 of the second embodiment are designated by the same reference numerals, and the descriptions thereon will be omitted.

A transparent heater plate 513 of glass of the lid 510 of the incubator 511 does not have a central aperture, and a transparent heater 517 of glass of the heater plate 515 has therein a hole 519 for accepting the lens of the microscope.

A means for securing the specimen i.e. a weight 521 of stainless steel is a ring, which is slightly larger in its diameter than that of the dish 313.

The weight 521 is served to depress the rising of the dish while the observation is effected by interposing any oil or water between the bottom surface of the dish 313 and the objective lens (T).

An incubator assembly for observation by microscope comprises the weight 521 and the incubator 511.

The method for using the incubator 511 of the third embodiment will now be described.

The weight 521 is placed on the dish 313 placed within the confine of the container-accommodating portion 392. Some oil is applied to the tip of the objective lens (T) and then the objective lens (T) is moved toward the dish 313 to make the oil layer between them. The observation of the specimen in the dish 313 such as cells is then effected.

The operation for shifting the dish 313 in order to change the area of the specimen in the dish 313 to be observed will now be described.

When it is intended to displace the dish 313 in the A-B direction, the presser screws 385 of the pair of left and right displacing mechanisms 350 and 352 of the means for displacing the specimen container are loosened to enable the shaft 387 to be displaced. Then the container holder 351 is displaced together with the shaft 387 in the A-B direction through the vertical portion 391 of the control member 389 to push the dish 313 through the holder 351 to shift the dish in the A direction or the B direction to a desired position. Then the screws 385 are fastened to hold the shafts 387 by the tips thereof to secure the position of the holder 351. In the conditions, the dish 313 is interposed between the rectangular shaped recesses provided at the tips 395 of the holders 351.

When it is intended to displace the dish 313 in the C-D direction, the presser screws 385 are fastened to hold the shafts 387 by the tips thereof to secure the positions of the pair of holders 351 to hold the dish 313. Then the presser screws 402 are loosened to release the tips of the screws 402 from the upwardly extending portions 377 to enable the slider 371 to shift in the C-D direction. Subsequently, the slider 371, the shaft 387, and the container holder 351 are displaced in the C direction or the D direction to a desired position by means of the control members 389 of the pair of left and right displacing mechanisms 350 and 352.

As can be seen from the above, even if observation is effected by the inverted microscope in which the objective lens (T) are directed to the dish 313 from the lower side of thereof, the position of the dish 313 can be changed from the outside of the unit 347, and the position of the area of the dish 313 to be observed can also be changed without removing the lid 510.

The fogging of the transparent heater plate 513 of the lid 510 caused by the generated steam may be prevented by the heat generated thereby so that the observation can be effected under the clear plate.

The transparent heater 329 of glass is secured on the lower surface of the inner flange 327. That is, it is depend therefrom.

Accordingly, the heater plate 317 expands or deforms downwardly upon heated by the heater 329. Further, there is a space between the plate 329 and the top plate 328. As a result, the expansion or deformation of the heater 329 does not affect the top plate 328.

Consequently, the dish 313 containing the specimen is prevented from moving along an optic axis of the objective lens (T). Thus the distance between the specimen to be observed and the objective lens (T) can be maintained constant to prevent the observed image from unclear.

While particular embodiments of the present invention have been illustrated and described, it should be obvious to those skilled in the art that various changes and modifications can be made without departing from the spirit and scope of the invention.

In the first embodiment, although the dish 220 with the cover 223 is used, the dish 220 may fit into the container-accommodating portion 205g without the cover 223. In the conditions, drugs or chemicals are introduced, after removing the cover 223, by inserting some tool through the work hole 245 of the heater plate 243, so that the operation can be effected without affecting the conditions such as the temperature within the space 235.

In the first embodiment, described is the circulation incubation by withdrawing the predetermined amount of nutrient medium through the tube 231 and at the same time delivering the same amount of nutrient medium through the tube 229. However, the present invention will not limited to such a structure, and a stationary incubation without requiring the exchange of nutrient medium may be made. In such a case, tubes 229 and 231 are omitted.

Further, the structure with no water supplying means such as water supplying pipe 213 and the infusion reservoir 216 may be employed. In such structure, water is supplied at first into the reservoir 205e and does not supplied additionally. This is because the incubation can be carried out for about 48 hours without supplying water. The window 239 formed through the lid plate 237 may be a rectangular configuration rather than a circular configuration.

In the first embodiment, the heater plate 259 includes at its center a through hole, and has the upper plate 275 of aluminum material. However, the structure of the heater cannot be limited to such structure. For example, the heater including a transparent conductive film deposited on the surface of the glass plate may be used.

There may be provided without the work hole 245 through the heater plate 243.

Although the dish 220 is placed on the top plate 271 in the first embodiment, the dish may be placed directly on the upper plate 275 with removing the top plate 271.

In order to avoid the observed image to be blurred through deformation of the upper and/or lower plates 275 and/or 277 in micron order by depriving the heater plate 259 of its heat energy through the contact with the objective lens (T), a lens heater may be wound around the cylindrical body of the objective lens (T).

In the second and third embodiments, the means for displacing the specimen container includes a pair of left and right displacing mechanisms 350 and 352, so that it is necessary to manipulate both mechanisms for shifting the dish 313. However, the dish maybe held in cantilever fashion by only one mechanism. In such case, the manipulation of the dish is made by the one mechanism.

Although the weight 521 is used to secure the specimen container in the third embodiment, the present invention is not limited thereto. Any means other than the weight such as spring can be used for securing the container and preventing it from rising.

The top plates 271 and 328 may be made of brass material. In such a case, it is necessary to provide a hole on the central portion of the top plate for transmitting the light ray therethrough. Further, the frame 261 of the heater plate 259 and the frame 525 and the heater plate 317 can also be made of brass material.

Although the heater plates 317 and 515 including a transparent heater element of glass are illustrated in the second and third embodiments, other heating means such as the heater plate 259 including a nichrome wire as a heating element may also be used.

In the above-mentioned embodiments, the incubator assembly comprises the combinations of the dish 220 and the incubator 201, the jig for securing the fixtures and the incubator 201, the dish tongs 461 and the incubator 311, or the weight 521 and the incubator 511. However, the assembly are not limited to the above recited combinations, and the incubator 201, 311 or 511 can be combined with either of the dish 220, the jig, the dish tongs 461, or the weight 521 as desired. Further, the assembly may comprise either one of the incubator 201, 311 or 511 and one or two or more of the dish 220, the jig, the dish tongs 461, or the weight 521. When it is desired to combine the jig with the incubator 311 or 511, the configuration of the outer jig member 294 may be varied to that of the water tank unit 347.

INDUSTRIAL APPLICABILITY

The incubator of the present invention will provide following advantages.

Incubation and observation of the specimen can be carried out on the stage of microscope.

Any manipulations or operations can be easily effected on the specimen without breaking the predetermined incubation conditions.

The portion of the specimen in the container to be observed by the microscope can be changed without breaking the predetermined incubation conditions.

Sufficient amount of vapor can be generated quickly within the incubation space.

What is claimed is:

1. An incubator for observation by microscope comprising:
    an upwardly water tank unit including a container-accommodating portion in which a specimen container is placed removably at the central portion thereof and a water reservoir disposed around the container-accommodating portion;
    a lid for covering the upper end of the unit;
    a heater for heating the specimen container and the unit; and
    a means for supplying gas into an incubation space defined by the unit and the lid;
    wherein:
        each of the unit and the lid have, at the central portion thereof, a light ray transmitting portion for transmitting light rays upwardly or downwardly therethrough;
        the heater is of a plate type heating the container from the bottom thereof, and the heater is also provided with a light ray transmitting portion at the position corresponding to those provided on the unit and the lid;
        the heater has a laminate comprising upper and lower plates and a heating element interposed therebetween, a top plate disposed above the upper plate with a space from the upper plate, and a frame for supporting the laminate and the top plate; and the top plate is isolated from the upper plate of the laminate and no surface of the top plate directly contacts any surface of the upper plate.

2. The incubator according to claim 1, wherein the top plate is rested on an inner flange of the frame.

3. An incubator for observation by microscope comprising:
an upwardly water tank unit including a container-accommodating portion in which a specimen container is placed removably at the central portion thereof and a water reservoir disposed around the container-accommodating portion;
a lid for covering the upper end of the unit;
a heater for heating the specimen container and the unit from the bottom thereof; and
a means for supplying gas into an incubation space defined by the unit and the lid;
wherein:
each of the unit and the lid have at the central portion thereof a light ray transmitting portion for transmitting light rays upwardly or downwardly therethrough;
the unit is adapted to be placed on the upper surface of a stage of the microscope so as not to contact with the heater with a spacing defined therebetween, and the unit and the heater are separable;
the heater is of a plate type; and
the upwardly water tank unit is isolated from the heater such that no part of the water reservoir is in direct contact with a top plate of the heater.

4. The incubator according to claim 3, further comprising fixtures for securing the unit on the upper surface to the stage of the microscope.

5. An incubator assembly for observation by microscope, comprising the incubator according to claim 4, and a jig assembly for securing the fixtures for the incubator in a desired position including a centering member and an outer jig member;
the centering member aligning the center of the water tank unit with the center of a tool fitting hole,
the outer jig member is fit around the peripheral portion of the unit, when the center of the water tank unit is aligned with the center of a tool fitting hole by the centering member, so that the fixtures are in contact and fit around the outer jig member for positioning.

6. The incubator according to claim 1, further comprising a means for supplying water into the reservoir from the outside of the unit.

7. The incubator according to claim 1, further comprising a nutrient medium supplying means for supplying nutrient medium into the container within the unit from outside thereof.

8. The incubator according to claim 7, wherein the nutrient medium supplying means has a structure for enabling the replenishment of nutrient medium within the container without removing the lid of the unit.

9. The incubator according to claim 1, the container-accommodating portion further comprising a pair of container holders disposed across the central portion of the unit, the spacing between the holders being adjustable.

10. The incubator according to claim 1, wherein an entrance opening is provided through a side wall of the unit for putting the container into and out of the accommodating portion, and a side closure member for closing and opening the entrance is also provided.

11. The incubator according to claim 1, wherein the lid covering the upper end of the unit has one or more slots formed through which any operation will be carried out to the specimen, the position of each slot is offset from the region of the accommodating portion on which the specimen container is to be placed, the lid is adjusted to shift, while closing still the opening on the upper end of the unit, to displace the slots directly above the region of the accommodating portion on which the specimen container is to be placed.

12. The incubator according to claim 1, wherein the lid covering the upper end of the unit has an aperture formed in the region of the accommodating portion on which the specimen container is to be placed, the aperture is covered with a cover plate being rested on the lid, the cover plate can be displaced relative to the upper surface of the lid within a predetermined range while closing the aperture, the cover plate has a hole formed therein for inserting an objective lens.

13. The incubator according to claim 1, wherein on the bottom surface of the water tank is provided a water tank heater.

14. The incubator according to claim 1, wherein the heater for heating the specimen container and the water tank unit has a container-placing portion at which a heating portion is formed of a transparent conductive film.

15. An incubator assembly for observation by microscope, comprising:
the incubator according to claim 1; and
a specimen container accommodated within the incubator;
wherein:
the specimen container includes a body opened at its upper surface and a lid for covering the upper surface;
the lid is provided integrally with a pair of protrusions for connecting tubes at its upper surface; and
the protrusion includes an aperture for connecting the tube, a channel extending from the aperture to the lower surface of the lid.

16. An incubator assembly according to claim 15, further comprising a means for securing the specimen container to urge the container against an objective lens of the microscope, when interposing any oil or water between the objective lens and the specimen container, and
the heater has a through hole.

17. An incubator assembly for observation by microscope, comprising:
the incubator according to claim 10; and
tongs for putting the specimen container into and out of the incubator;
wherein the tongs include a pair of arms formed of elastically deformable material connected at the rear ends or proximal ends thereof, which arms are crossed with each other at a crossing portion provided through a middle portion of these arms, and include a pair of urging portions to have the arms approach each other and close by the force generated by the elastic deformation of the material of the tongs, and a pair of parallel pinching portions made between the urging portions and the crossing portions, preventing the urging portions to be removed in a closing direction.

* * * * *